(12) United States Patent
Polniaszek et al.

(10) Patent No.: US 9,115,100 B2
(45) Date of Patent: Aug. 25, 2015

(54) METHODS AND INTERMEDIATES FOR PREPARING PHARMACEUTICAL AGENTS

(71) Applicant: Gilead Sciences, Inc., Foster City, CA (US)

(72) Inventors: Richard Polniaszek, Half Moon Bay, CA (US); Steven Pfeiffer, Camarillo, CA (US); Richard Yu, San Francisco, CA (US); Aaron Cullen, Mililani, HI (US); Eric Dowdy, White Rock, NM (US); Duong Tran, Alberta (CA); Kenneth Kent, Sunnyvale, CA (US); Zhongxin Zhou, Alberta (CA); Doug Cordeau, Ithaca, NY (US); Leah Easton-Scott, San Mateo, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 14/476,622

(22) Filed: Sep. 3, 2014

(65) Prior Publication Data

US 2015/0005493 A1    Jan. 1, 2015

Related U.S. Application Data

(62) Division of application No. 13/925,302, filed on Jun. 24, 2013, now Pat. No. 8,853,210, which is a division of application No. 12/752,639, filed on Apr. 1, 2010, now Pat. No. 8,497,396.

(60) Provisional application No. 61/166,498, filed on Apr. 3, 2009.

(51) Int. Cl.
| | |
|---|---|
| *C07C 307/02* | (2006.01) |
| *C07C 307/06* | (2006.01) |
| *C07D 417/12* | (2006.01) |
| *C07D 277/30* | (2006.01) |
| *C07D 413/12* | (2006.01) |
| *C07D 413/14* | (2006.01) |
| *C07D 417/14* | (2006.01) |
| *C07C 209/62* | (2006.01) |
| *C07C 209/70* | (2006.01) |
| *C07D 277/28* | (2006.01) |
| *C07C 303/34* | (2006.01) |

(52) U.S. Cl.
CPC ............ *C07D 277/30* (2013.01); *C07C 209/62* (2013.01); *C07C 209/70* (2013.01); *C07C 303/34* (2013.01); *C07C 307/02* (2013.01); *C07C 307/06* (2013.01); *C07D 277/28* (2013.01); *C07D 413/12* (2013.01); *C07D 413/14* (2013.01); *C07D 417/12* (2013.01); *C07D 417/14* (2013.01)

(58) Field of Classification Search
None
See application file for complete search history.

(56) References Cited

U.S. PATENT DOCUMENTS

| | | | |
|---|---|---|---|
| 7,939,553 B2 | 5/2011 | Desai et al. | |
| 8,497,396 B2 | 7/2013 | Polniaszek et al. | |
| 8,853,210 B2 | 10/2014 | Polniaszek et al. | |
| 2003/0153771 A1 | 8/2003 | Kolb et al. | |

FOREIGN PATENT DOCUMENTS

| | | |
|---|---|---|
| WO | WO-03/106445 A1 | 12/2003 |
| WO | WO-2008/010921 A2 | 1/2008 |
| WO | WO-2008/103949 A1 | 8/2008 |
| WO | WO-2010/115000 A2 | 10/2010 |
| WO | WO-2010/115000 A3 | 10/2010 |

OTHER PUBLICATIONS

Rao, et al., Tet. Lett., 36:2505 (1995).*
Duggan, M.E. et al. (1983). "Preparation of Optically Active 2-Aminoalkylphosphinic and Phosponic Acids," *Tetrahedron Letters* 24(29):2935-2938.
Gurjar, M.K. et al. (1997). "Synthesis of Novel $C_2$-Symmetric and Pseudo C2-Symmetric Based Diols, Epoxides and Dideoxy Derivatives of HIV Protease Inhibitors," *Tetrahedron* 53(13):4769-4778.
Hannam, J. et al. (2006). "Rapid and Selective Synthesis of Substituted 1,2,5-Thiadiazolidine 1,1-Dioxides," *Synlett.* 6:833-836.
Hiebl, J. et al. (1999). "Large-Scale Synthesis of Hematoregulatory Nonapeptide SK&F 107647 by Fragment Coupling," *J. Pept. Res.* 54(1):54-65.
Hodgson, D.M. et al. (2006). "Dimerization of Lithiated Terminal Aziridines," *Angew. Chem. Int. Ed.* 45(6):935-938.
Hodgson, D.M. et al. (Nov. 2007). "Dimerization and Isomerization Reactions of α-Lithiated Terminal Aziridines," *J. Org. Chem.* 72(26):10009-10021.
Mukai, T. et al. (Mar. 2008). "Synthesis of a β-Tetrapeptide Analog as a Mother Compound for the Development of Matrix Metalloproteinase-2-Imaging Agents," *Chem. & Pharmaceutical Bulletin* 56(3):260-265.

(Continued)

*Primary Examiner* — Michael Barker
(74) *Attorney, Agent, or Firm* — Joel B. Silver

(57) ABSTRACT

The invention provides methods and intermediates that are useful for preparing a compound of formula I:

and salts thereof.

4 Claims, No Drawings

(56) References Cited

OTHER PUBLICATIONS

Natelson, S. et al. (1989). "Preparation of D-, DL-, and L-Homoserine Lactone from Methionine," *Microchemical Journal* 40(2):226-232.
Olah, G.A. et al. (1982). "Iodotrimethylsilane-A Versatile Synthetic Reagent," *Tetrahedron* 38(15):2225-2277.
Spaltenstein, A. et al. (1987). "New Approaches to the Synthesis of *tran-Alkene* Isosteres of Dipeptides," *J. Org. Chem.* 52(17):3759-3766.
Wuts, P.G.M. et al. (Dec. 2006). *Greene's Protective Groups in Organic Synthesis*, 4th Edition, John Wiley & Sons, Inc., pp. 851-852.
Wuts, P.G.M. et al. (Dec. 2006). *Greene's Protective Groups in Organic Synthesis*, 4th Edition, John Wiley & Sons, Inc., pp. 872-873.
Xu, L. et al. (Feb. 4, 2009). "A Novel and Efficient Synthesis of Chiral $C_2$-Symmetric 1,4-Diamines," *Tetrahedron Letters* 50(5):552-554.
Notice of Allowance mailed on Mar. 31, 2014, for U.S. Appl. No. 13/925,302, filed Jun. 24, 2013, seven pages.
Notice of Allowance mailed on Jun. 3, 2014, for U.S. Appl. No. 13/925,302, filed Jun. 24, 2013, seven pages.
Bolivian Office Action mailed on May 29, 2014, for Bolivian Patent Application No. SP-0082-2010, filed on Apr. 1, 2010, six pages.
Canadian Office Action mailed on Feb. 11, 2014, for Canadian Patent Application No. 2,754,698, filed on Apr. 1, 2010, two pages.
Chilean Office Action mailed on Sep. 15, 2014, for Chilean Patent Application No. 23702011, filed on Apr. 1, 2010, ten pages.
Chinese Office Action mailed on Jan. 23, 2014, for Chinese Patent Application No. 201080014307.7, filed on Apr. 1, 2010, six pages.
Chinese Office Action mailed on Jun. 8, 2013, for Chinese Patent Application No. 201080014307.7, filed on Apr. 1, 2010, twenty-five pages.
Chinese Office Action mailed on Jul. 8, 2014, for Chinese Patent Application No. 201080014307.7, filed on Apr. 1, 2010, seven pages.
Columbian Office Action mailed on Nov. 6, 2013, for Columbian Patent Application No. 11114749, filed on Apr. 1, 2010, twelve pages.
Columbian Office Action mailed on Mar. 4, 2014, for Columbian Patent Application No. 11114749, filed on Apr. 1, 2010, ten pages.
Eurasian Office Action mailed on Jan. 31, 2014, for Eurasian Patent Application No. 201190179, filed on Apr. 1, 2010, five pages.
Eurasian Office Action mailed on Aug. 8, 2014, for Eurasian Patent Application No. 201190179, filed on Apr. 1, 2010, four pages.
European Communication mailed on Nov. 29, 2012, for European Patent Application No. 10 713 075.9 filed on Apr. 1, 2010, five pages.
European Communication mailed on May 10, 2013, for European Patent Application No. 10 713 075.9 filed on Apr. 1, 2010, three pages.
European Communication mailed on Nov. 28, 2013, for European Patent Application No. 10 713 075.9 filed on Apr. 1, 2010, three pages.
Indonesian Office Action mailed on Jan. 10, 2014, for Indonesian Patent Application No. W00201103554, filed on Apr. 1, 2010, four pages.
International Preliminary Report on Patentability mailed on Oct. 13, 2011, for PCT Patent Application No. PCT/US2010/029633 filed on Apr. 1, 2010, seventeen pages.
International Search Report mailed on Jul. 22, 2011, for PCT Patent Application No. PCT/US2010/029633 filed on Apr. 1, 2010, seven pages.
Israeli Office Action mailed on Jul. 7, 2013, for Israeli Patent Application No. 215399, filed on Apr. 1, 2010, three pages.
Japanese Office Action mailed on Feb. 20, 2014, for Japanese Patent Application No. 2012-503704, filed on Apr. 1, 2010, seven pages.
New Zealand Office Action mailed on Jan. 22, 2014, for New Zealand Patent Application No. 594864, filed on Apr. 1, 2010, two pages.
New Zealand Office Action mailed on Aug. 17, 2012, for New Zealand Patent Application No. 594864, filed on Apr. 1, 2010, two pages.
New Zealand Office Action mailed on Nov. 22, 2013, for New Zealand Patent Application No. 617773, filed on Apr. 1, 2010, two pages.
Notice of Allowance mailed on Oct. 9, 2013, for African Regional Patent Application No. AP/P/2011/005864, filed on Apr. 1, 2010, five pages.
Notice of Allowance mailed on Sep. 2, 2013, for Mexican Patent Application No. MX/a/2011/010397, filed on Apr. 1, 2010, one page.
Peruvian Office Action mailed on Jan. 31, 2014, for Peruvian Patent Application No. 1737, filed on Apr. 1, 2010, ten pages.
Singapore Search Report mailed on Jan. 30, 2014, for Singapore Patent Application No. 201106993-7, filed on Apr. 1, 2010, eleven pages.
Singapore Written Opinion mailed on Jan. 30, 2014, for Singapore Patent Application No. 201106993-7, filed on Apr. 1, 2010, ten pages.
Taiwanese Office Action mailed on Dec. 19, 2013, for Taiwanese Patent Application No. 099109929, filed on Apr. 1, 2010, ten pages.
Written Opinion from the International Searching Authority mailed on Jul. 22, 2011, for PCT Patent Application No. PCT/US2010/029633 filed on Apr. 1, 2010, sixteen pages.
Canadian Office Action dated Oct. 24, 2014 for Canadian Patent Application No. 2,754,698.

\* cited by examiner

METHODS AND INTERMEDIATES FOR PREPARING PHARMACEUTICAL AGENTS

CROSS REFERENCE TO RELATED APPLICATIONS

This application is a divisional of U.S. application Ser. No. 13/925,302, filed Jun. 24, 2013, now U.S. Pat. No. 8,852,210, which is a divisional of U.S. application Ser. No. 12/752,639, filed Apr. 1, 2010, now U.S. Pat. No. 8,497,396, which claims priority benefit of Provisional Patent Application No. 61/166,498, filed Apr. 3, 2009, the contents of which are incorporated here by reference in their entirety.

BACKGROUND OF THE INVENTION

International Patent Application Publication Number WO 2008/010921 and International Patent Application Publication Number WO 2008/103949 disclose certain compounds that are reported to be useful to modify the pharmacokinetics of a co-administered drug, e.g. by inhibiting cytochrome P450 monooxygenase. One specific compound identified therein is a compound of the following formula I:

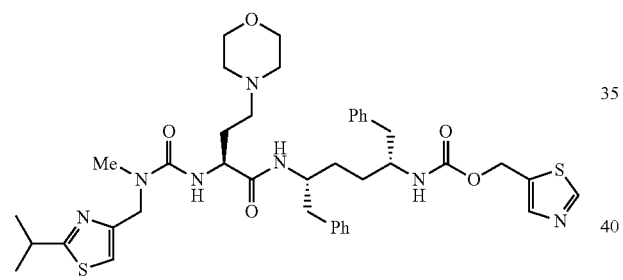

There is currently a need for improved synthetic methods and intermediates that can be used to prepare the compound of formula I and its salts. There is also a need for improved methods for preparing intermediate compounds that can be used to prepare the compound of formula I and its salts. The improved methods and intermediates may reduce the cost, time, and/or the amount of waste associated with the existing methods for preparing the compound of formula I and its salts.

SUMMARY OF THE INVENTION

An improved synthetic route for preparing the compound of formula I and its salts has been identified. This improved synthetic route utilizes novel intermediates of formulae IV, V, XIV, XVI, XVII, and XVIII, identified herein below.

This route reduces the cost, the time, and the amount of waste associated with the preparation of the compound of formula I and its salts.

Accordingly in one embodiment, the invention provides a compound of formula IV:

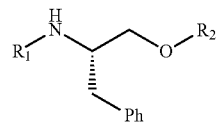

wherein $R_1$ and $R_2$ are each independently a suitable protecting group; or a salt thereof.

In another embodiment, the invention provides a compound of formula V:

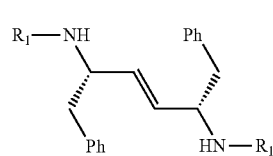

wherein each $R_1$ is a suitable protecting group other than tert-butylsulfonyl; or a salt thereof.

In another embodiment, the invention provides a compound of formula XIV:

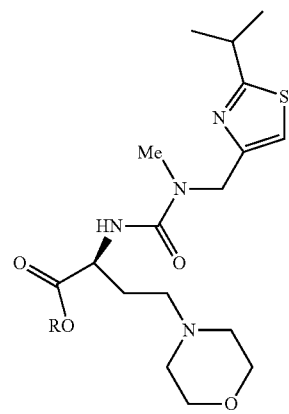

wherein R is $(C_2-C_8)$alkyl, or a salt thereof.

In another embodiment, the invention provides a method for preparing a compound of formula V:

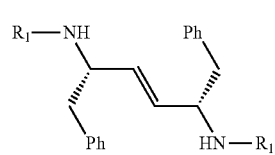

wherein each $R_1$ is a suitable protecting group other than tert-butylsulfonyl, or a salt thereof, comprising dimerizing a corresponding compound of formula II:

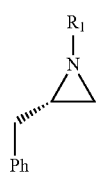

to provide the compound of formula V, or the salt thereof.

In another embodiment, the invention provides a method for preparing a compound of formula I:

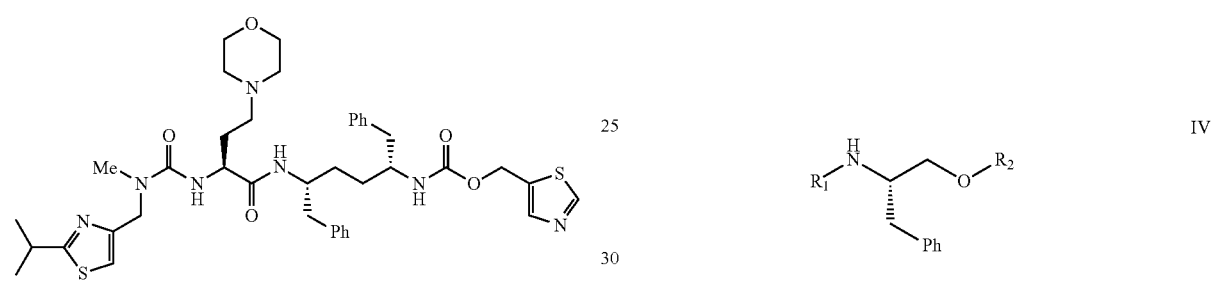

or a salt thereof, wherein a compound of formula V:

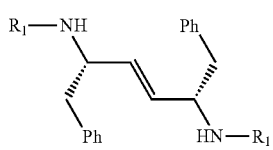

wherein $R_1$ is a suitable protecting group, or a salt thereof is prepared and converted into a compound of formula I, characterized in that the compound of formula V is prepared from a corresponding compound of formula II:

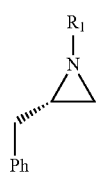

or a salt thereof, by dimerizing the compound of formula II.

In another embodiment, the invention provides a method for preparing a compound of formula I:

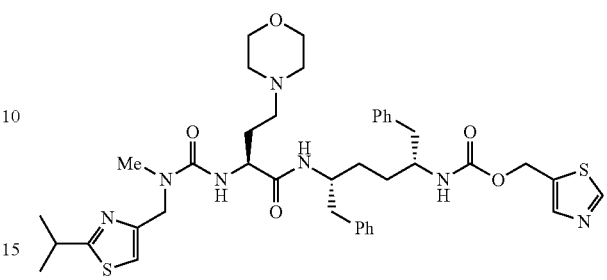

or a salt thereof, wherein a compound of formula IV:

wherein $R_1$ and $R_2$ are each independently a suitable protecting group, or a salt thereof is prepared and converted into a compound of formula I, characterized in that the compound of formula IV is prepared from a compound of formula III:

or a salt thereof, by protecting the compound of formula III.

In another embodiment, the invention provides a method for preparing a compound of formula I:

or a salt thereof, wherein a compound of formula XIV:

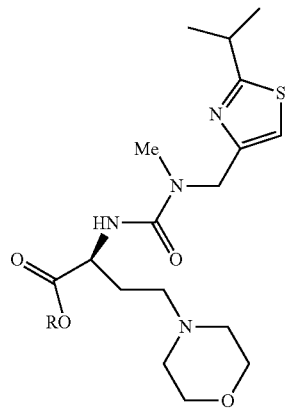

XIV wherein R is H or (C$_1$-C$_8$)alkyl, or a salt thereof is prepared and converted into a compound of formula I, characterized in that the compound of formula XIV or the salt thereof is prepared from a compound of formula XIII:

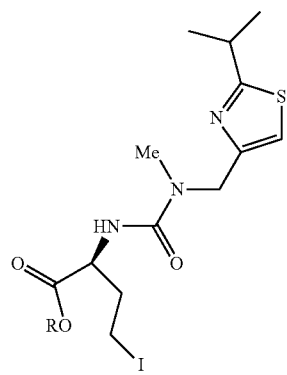

XIII wherein R is H or (C$_1$-C$_8$)alkyl or a salt thereof, by displacing the iodide with a suitable morpholine reagent. In a further embodiment of this method of the invention R is (C$_2$-C$_8$)alkyl in the compound of formula XIII and XIV.

In another embodiment, the invention provides a compound of formula XVI or XVII:

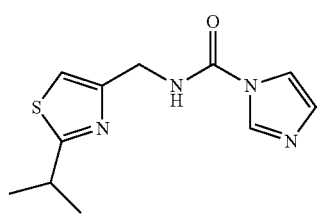

XVI or

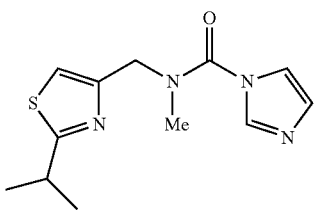

XVII or a salt thereof.

In another embodiment, the invention provides a salt of formula XVIII:

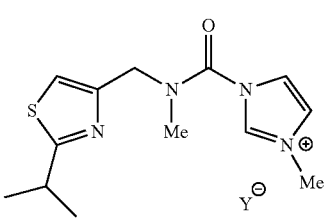

XVIII wherein Y$^-$ is a suitable counterion,

In another embodiment, the invention provides a method for preparing a compound of formula I:

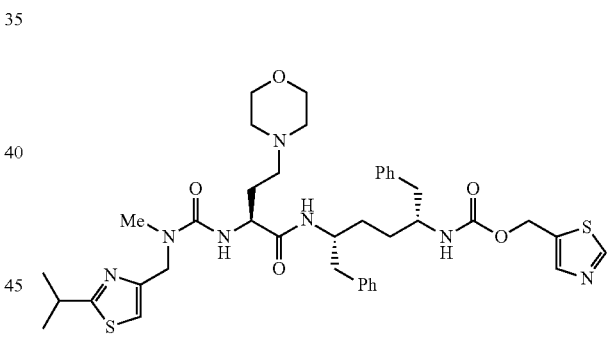

I or a salt thereof, wherein a compound of formula XII:

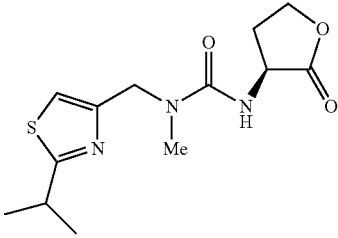

XII or a salt thereof is prepared and converted into a compound of formula I, characterized in that the compound of formula XII is prepared from a corresponding compound of formula XVIII:

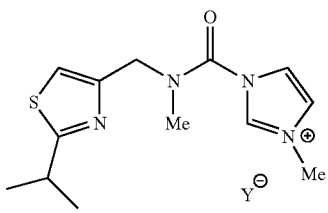

wherein Y⁻ is a suitable counterion, by treatment with a compound of formula XI:

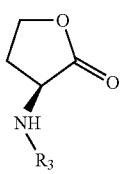

wherein R₃ is H or a protecting group in the presence of a base and optionally removing R₃ if it is a protecting group to provide the compound of formula XII.

In another embodiment, the invention provides a method for preparing a compound of formula I:

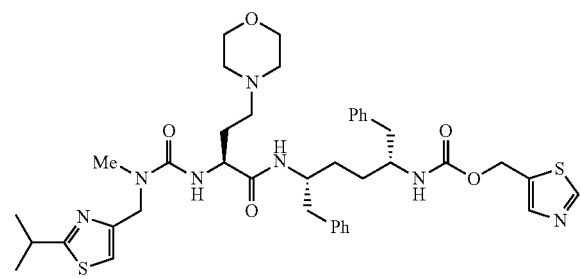

or a salt thereof, wherein a salt of formula XVIII:

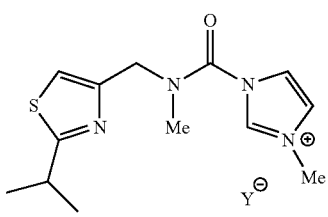

wherein Y⁻ is a suitable counterion is prepared and converted into a compound of formula I, characterized in that the salt of formula XVIII is prepared from a compound of formula XVII:

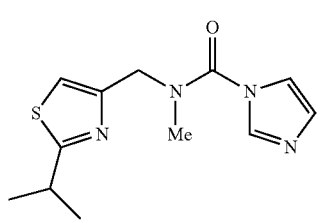

or a salt thereof by treatment with a methylating agent to provide the salt of formula XVIII.

In another embodiment, the invention provides a method for preparing a compound of formula I:

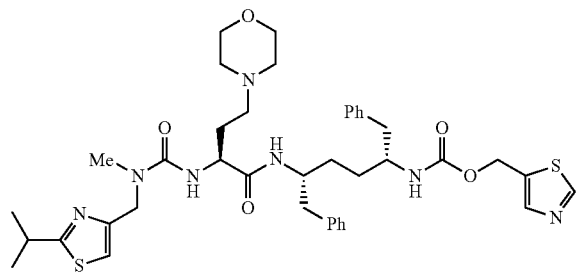

or a salt thereof, wherein a compound of formula XVII:

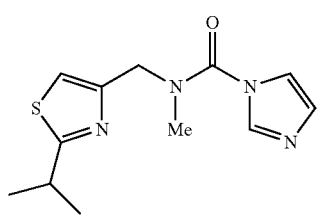

or a salt thereof is prepared and converted into a compound of formula I, characterized in that the compound of formula XVII is prepared from a corresponding compound of formula XVI:

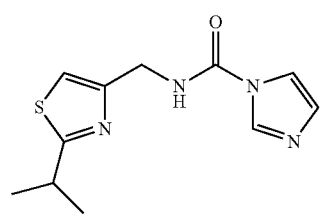

or a salt thereof by treatment with a methylating agent to provide the compound of formula XVII or the salt thereof.

In another embodiment, the invention provides a method for preparing a compound of formula I:

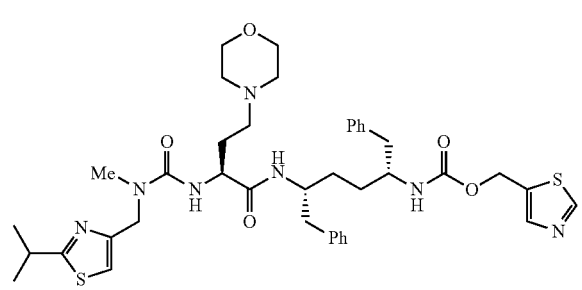

or a salt thereof, wherein a compound of formula XVI:

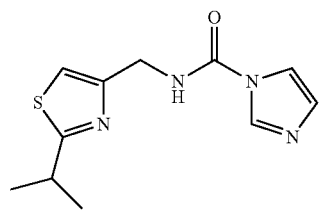

or a salt thereof is prepared and converted into a compound of formula I, characterized in that the compound of formula XVI is prepared from a corresponding compound of formula XV:

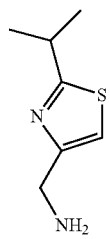

or a salt thereof by treatment with carbonyldiimidazole in the presence of a base to provide the compound of formula XVI.

In another embodiment, the invention provides a method (Method A) for preparing a compound of formula I:

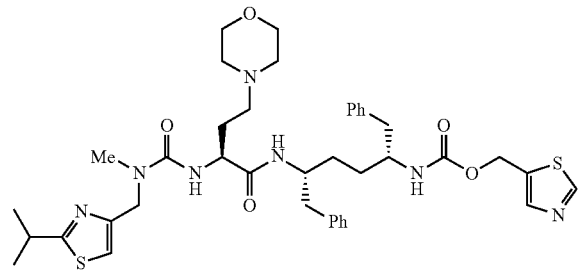

or a salt thereof comprising:

a) dimerizing a corresponding compound of formula II:

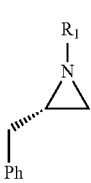

wherein $R_1$ is a suitable protecting group to provide a corresponding compound of formula V:

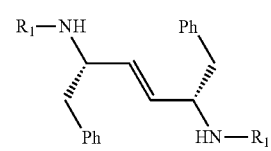

or a salt thereof;

b) deprotecting the compound of formula V or the salt thereof to provide a compound of formula VI:

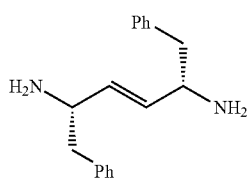

or a salt thereof;

c) reducing the compound of formula VI or the salt thereof to a compound of formula VII:

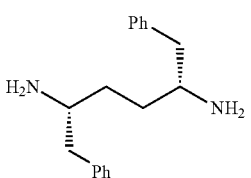

or a salt thereof;

d) converting the compound of formula VII to a corresponding salt by treatment with an acid in an organic solvent;

e) converting the corresponding salt from d) to a compound of formula IX:

IX

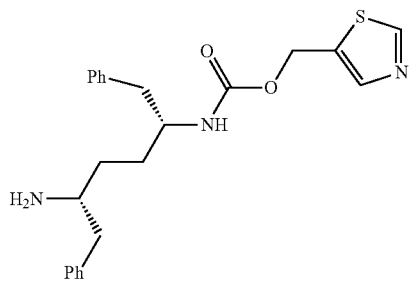

or a salt thereof (e.g. a mineral acid salt such as an HCl salt); and f) coupling the compound of formula IX or the salt thereof with a salt of formula X:

X

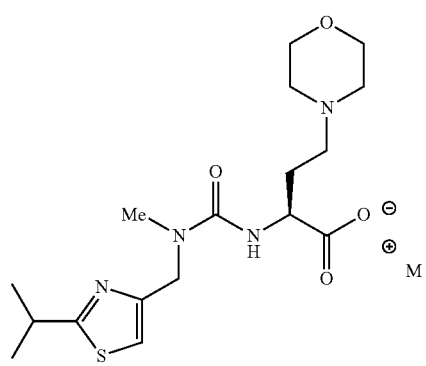

wherein M$^+$ is a suitable counterion to provide the compound of formula I. In one specific embodiment of the invention a salt of the compound of formula IX (e.g. an HCl salt) can be coupled with a salt of formula X to provide the compound of formula I.

In another embodiment, Method A can further comprise preparing the compound of formula II by reacting (S)-2-benzylaziridine with a corresponding compound $R_1$—X, wherein X is a leaving group (e.g. Cl) to provide the compound of formula II.

In another embodiment, Method A can further comprise preparing the compound of formula II by:

a) protecting a compound of formula III:

III

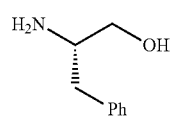

or a salt thereof to provide a corresponding compound of formula IV:

IV

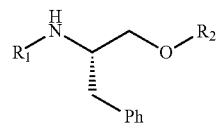

wherein $R_1$ and $R_2$ are each independently a suitable protecting group, or a salt thereof; and b) treating the compound of formula IV or the salt thereof with a suitable base to provide the compound of formula II.

In another embodiment, Method A can further comprise preparing the salt of formula X by:

a) treating a compound of formula XII:

XII

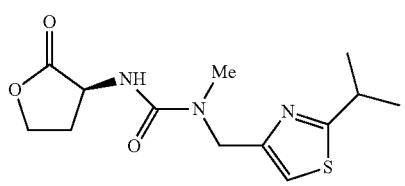

or a salt thereof with a suitable iodide source in the presence of an alcohol ROH to provide a compound of formula XIII:

XIII

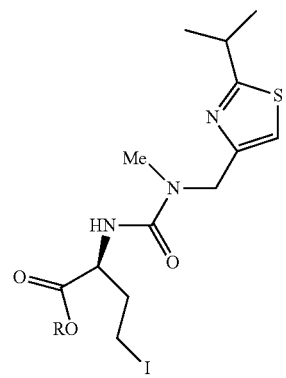

wherein R is (C$_1$-C$_8$)alkyl, or a salt thereof;

b) treating the compound of formula XIII or the salt thereof with morpholine to provide an ester of formula XIV:

XIV

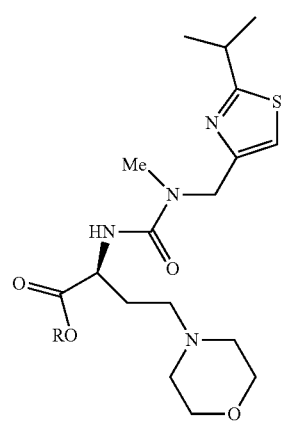

or a salt thereof; and c) hydrolyzing the ester of formula XIV to provide the salt of formula X.

In another embodiment, Method A can further comprise preparing the compound of formula XII or the salt thereof by:

a) treating L-methionine with an alkylating agent and optionally protecting the resulting amine to provide an amine of formula XI:

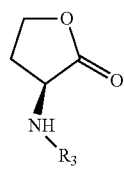

XI wherein $R_3$ is H or a protecting group, or a salt thereof; and b) treating the amine of formula XI or the salt thereof with a compound of formula XIX:

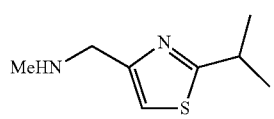

XIX or a salt thereof to provide the compound of formula XII or the salt thereof.

In another embodiment, Method A can further comprise preparing the compound of formula XII or the salt thereof by:

a) treating a compound of formula XV:

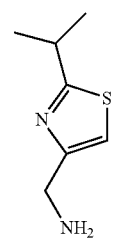

XV or a salt thereof with carbonyldiimidazole in the presence of a base to provide a compound of formula XVI:

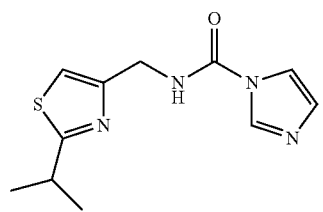

XVI or a salt thereof;

b) treating the compound of formula XVI or the salt thereof with a suitable methylating agent in the presence of a base to provide a compound of formula XVII:

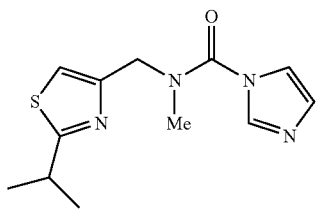

XVII or a salt thereof;

c) methylating the compound of formula XVII or the salt thereof to provide a salt of formula XVIII:

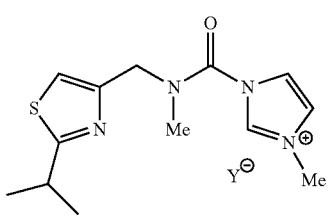

XVIII wherein $Y^-$ is a suitable counterion; and d) treating the salt of formula XVIII with an amine of formula XI:

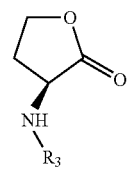

XI wherein $R_3$ is H or a protecting group, or a salt thereof with a suitable base, and deprotecting to remove $R_3$ if it is a protecting group, to provide the compound of formula XII or the salt thereof.

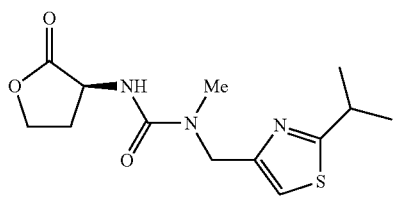

XII

The invention also provides novel synthetic intermediates described herein as well as methods for preparing such intermediates.

DETAILED DESCRIPTION

As used herein alkyl, alkoxy, etc. denote both straight and branched groups; but reference to an individual radical such as propyl embraces only the straight chain radical, a branched chain isomer such as isopropyl being specifically referred to. Haloalkyl denotes an alkyl group that is substituted with one or more (e.g. 1, 2, 3, 4, etc.) halo groups. Aryl denotes a phenyl radical or an ortho-fused bicyclic carbocyclic radical having about nine to ten ring atoms in which at least one ring is aromatic.

Specific values listed below for radicals, substituents, and ranges, are for illustration only; they do not exclude other defined values or other values within defined ranges for the radicals and substituents.

Specifically, $(C_1-C_8)$alkyl can be methyl, ethyl, propyl, isopropyl, butyl, iso-butyl, sec-butyl, pentyl, 3-pentyl, hexyl, heptyl, or octyl; $(C_1-C_8)$alkoxy can be methoxy, ethoxy, propoxy, isopropoxy, butoxy, iso-butoxy, sec-butoxy, pentoxy, hexyloxy, heptyloxy, or octyloxy; halo$(C_1-C_8)$alkyl can be fluoromethyl, difluoromethyl, and trifluoromethyl; aryl-$(C_1-C_8)$alkoxy can be benzyloxy; and aryl can be phenyl, indenyl, or naphthyl.

A specific value for $R_1$ is an N,N-disubstituted aminosulfonyl group.

Another specific value for $R_1$ is an N,N-dialkyl aminosulfonyl group.

Another specific value for $R_1$ is —S(=O)$_2$NR$_a$R$_b$, —S(=O)$_2$R$_c$, —C(=O)R$_c$, or —C(=O)NR$_a$R$_b$ wherein each of R$_a$ and R$_b$ is independently $(C_1-C_8)$alkyl; or R$_a$ and R$_b$ together with the nitrogen to which they are attached form a 3 or 4 membered saturated ring or a 5, 6, or 7 membered saturated or partially unsaturated ring comprising 1 or 2 heteroatoms (e.g. aziridine, azetidine, piperidine, morpholine, thiomorpholine, pyrrolidine, homopiperazine, homopiperidine, or piperazine); and R$_c$ is aryl, $(C_1-C_8)$alkyl, halo$(C_1-C_8)$ alkyl $(C_1-C_8)$alkoxy, or aryl-$(C_1-C_8)$alkoxy, wherein any aryl can optionally be substituted with one or more $(C_1-C_8)$alkyl. In one embodiment of the invention $R_1$ is not tert-butylsulfonyl (e.g. for a compound of formula V).

Another specific value for $R_1$ is —S(=O)$_2$NR$_a$R$_b$ wherein each of R$_a$ and R$_b$ is independently $(C_1-C_8)$alkyl; or R$_a$ and R$_b$ together with the nitrogen to which they are attached form a 3 or 4 membered saturated ring or a 5, 6, or 7 membered saturated or partially unsaturated ring comprising 1 or 2 heteroatoms (e.g. aziridine, azetidine, piperidine, morpholine, thiomorpholine, pyrrolidine, homopiperazine, homopiperidine, or piperazine.)

Another specific value for $R_1$ is:

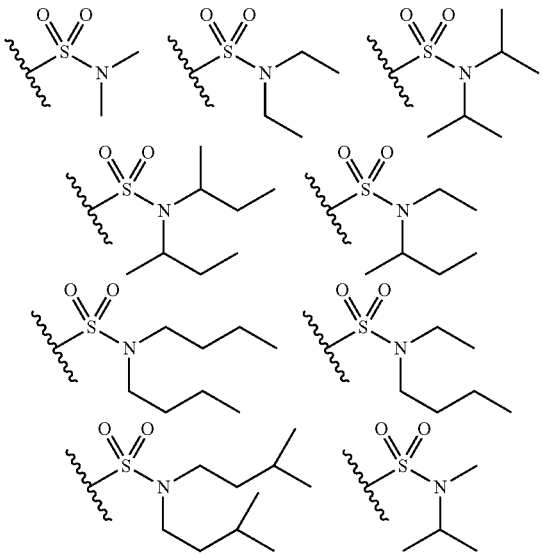

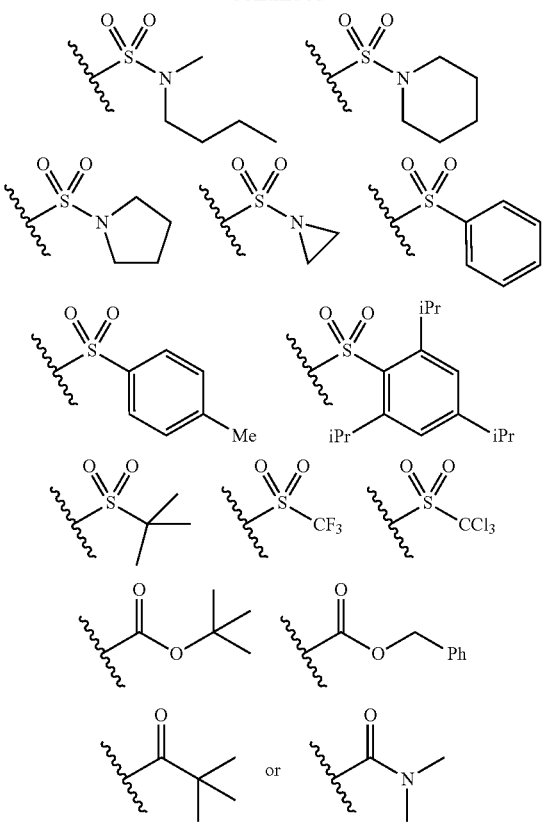

Another specific value for $R_1$ is —S(O)$_2$N(CH$_3$)$_2$.

Another specific value for $R_1$ is benzyloxycarbonyl.

A specific value for $R_2$ is an N,N-disubstituted aminosulfonyl group.

Another specific value for $R_2$ is an N,N-dialkyl aminosulfonyl group.

Another specific value for $R_2$ is —S(=O)$_2$NR$_a$R$_b$, —S(=O)$_2$R$_c$, —C(=O)R$_c$, or —C(=O)NR$_a$R$_b$ wherein each of R$_a$ and R$_b$ is independently $(C_1-C_8)$alkyl; or R$_a$ and R$_b$ together with the nitrogen to which they are attached form a 3 or 4 membered saturated ring or a 5, 6, or 7 membered saturated or partially unsaturated ring comprising 1 or 2 heteroatoms (e.g. aziridine, azetidine, piperidine, morpholine, thiomorpholine, pyrrolidine, homopiperazine, homopiperidine, or piperazine); and R$_c$ is aryl, $(C_1-C_8)$alkyl, halo$(C_1-C_8)$ alkyl $(C_1-C_8)$alkoxy, or aryl-$(C_1-C_8)$alkoxy, wherein any aryl can optionally be substituted with one or more $(C_1-C_8)$alkyl.

Another specific value for $R_2$ is —S(=O)$_2$NR$_d$R$_e$ wherein each of R$_d$ and R$_e$ is independently $(C_1-C_8)$alkyl; or R$_d$ and R$_e$ together with the nitrogen to which they are attached form a 3 or 4 membered saturated ring or a 5, 6, or 7 membered saturated or partially unsaturated ring comprising 1 or 2 heteroatoms (e.g. aziridine, azetidine, piperidine, morpholine, thiomorpholine, pyrrolidine, homopiperazine, homopiperidine, or piperazine.

Another specific value for $R_2$ is a leaving group such as 4-methylphenyl-sulfonyl, methylsulfonyl, trifluoromethylsulfonyl.

Another specific value for R₂ is:
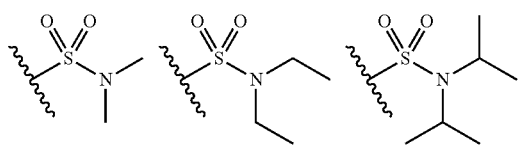
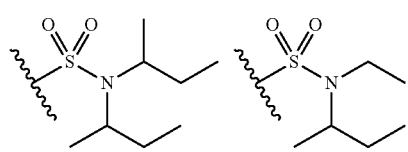
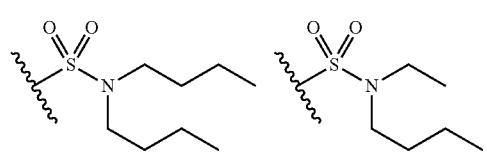
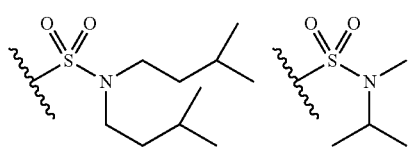
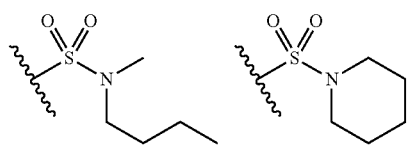
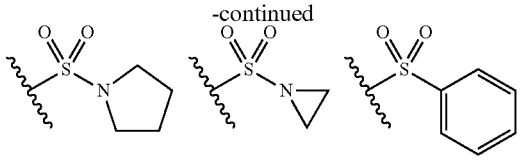
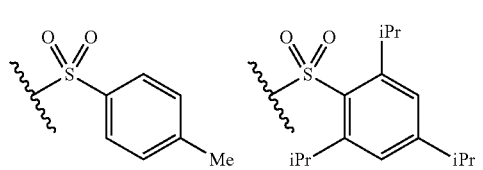
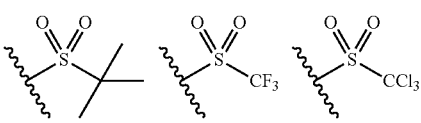
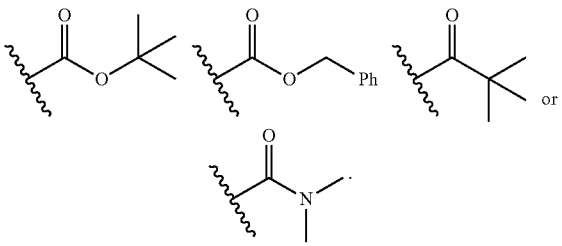
or
A specific value for R³ is H.
A compound of formula I or a salt thereof can be prepared as illustrated in Schemes 1-4 below.
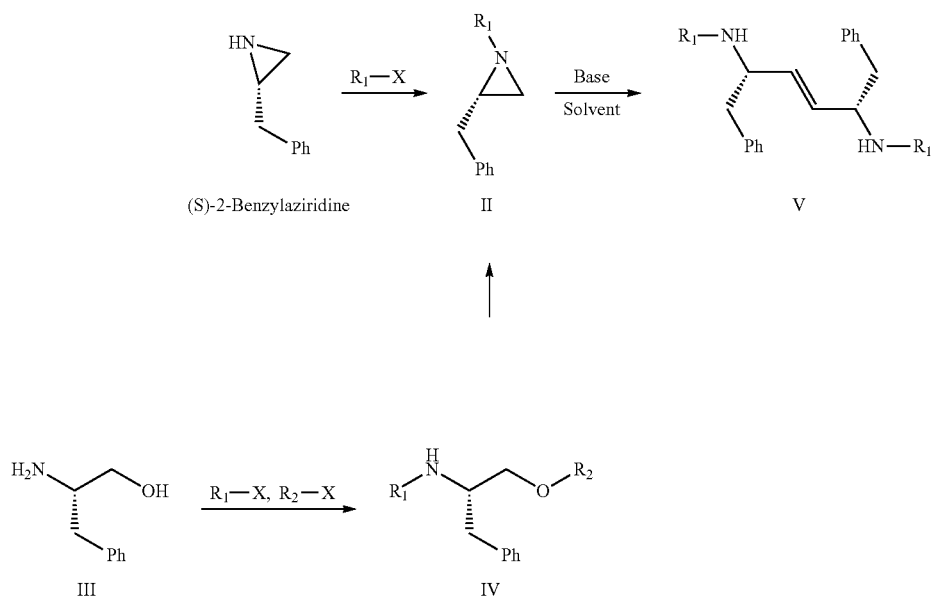

Scheme 2
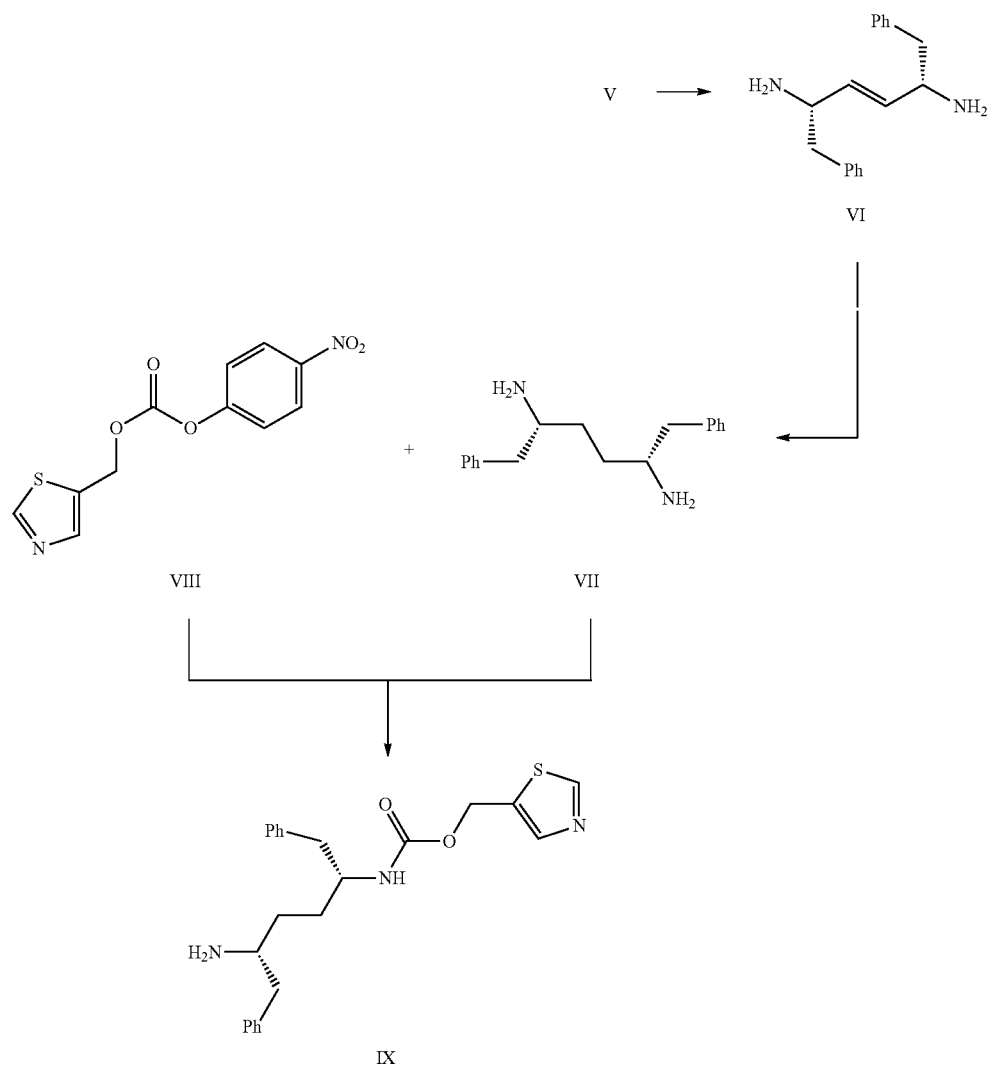
Scheme 3
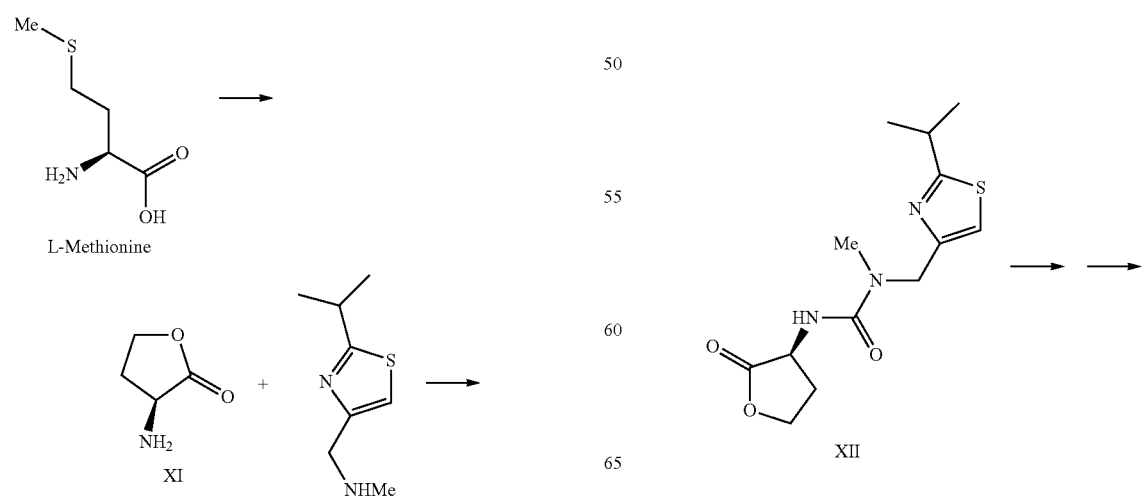

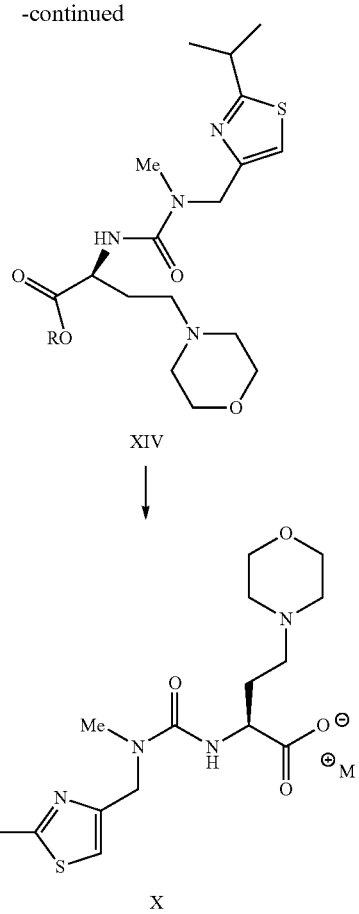

XIV

↓

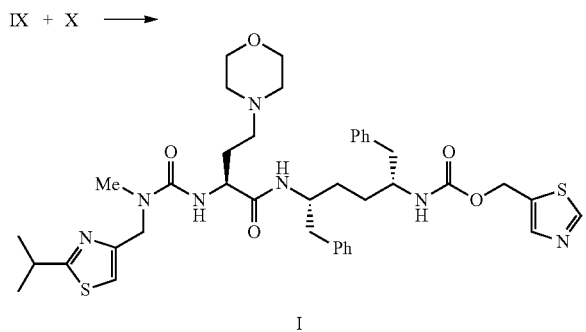

X

Scheme 4

IX + X →

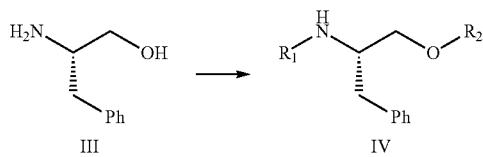

I

Preparation of a Compound of Formula IV

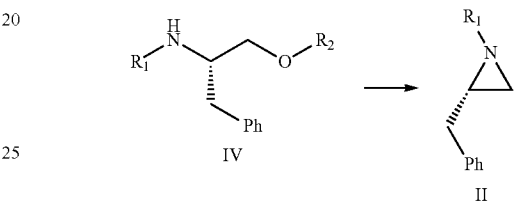

A compound of formula III can be protected with any suitable protecting groups ($R_1$ and $R_2$, which can be the same or different) under standard conditions to provide the corresponding compound of formula IV. For example, the reaction (s) can be carried out in a suitable solvent in the presence of a base. Suitable solvents include aprotic solvents such as, dichloromethane, tetrahydrofuran, and 2-methyltetrahydrofuran, as well as other aprotic organic solvents, and mixtures thereof. Suitable bases include trialkylamines, such as tri-ethylamine, diisopropylethylamine, and N-methyl morpholine, as well as hydride bases, such as sodium hydride. The reaction can conveniently be carried out at a temperature from about −20° C. to 40° C.

Suitable protecting groups include a tert-butylsulfonyl (Bus) group, N,N-dialkylsulfamoyl groups such as N,N-di-isopropylsulfamoyl, N-aziridinylsulfamoyl and other sulfamoyl groups containing an N-heterocycle (such as pyrrolidine or piperidine), as well as N-ethyl and N-methylsulfamoyl groups and other mixed N-alkylsulfamoyl groups.

Preparation of a Compound of Formula II

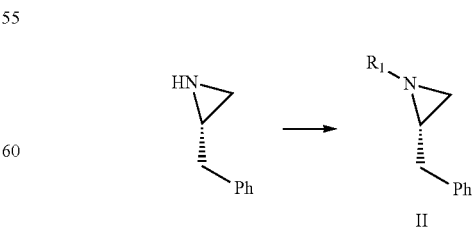

A compound of formula II can be prepared from a compound of formula IV by treatment with a base in a suitable solvent. Suitable bases include metal hydrides such as sodium hydride and potassium hydride; lithium 2,2,6,6-tetramethylpiperidide; the alkoxides, such as sodium tert-butoxide or lithium tert-butoxide, the hexamethyldisilazides, such as lithium hexamethyldisilazide, and carbonate bases, such as potassium carbonate or cesium carbonate.

Suitable solvents include aprotic solvents such as dichloromethane, tetrahydrofuran, and 2-methyltetrahydrofuran, as well as other aprotic organic solvents, and mixtures thereof. The reaction can conveniently be carried out at a temperature from about 0° C. to 22° C.

Suitable $R_1$ groups include a tert-butylsulfonyl (Bus) group, N,N-dialkylsulfamoyl groups such as N,N-diisopropylsulfamoyl, N-aziridinylsulfamoyl and other sulfamoyl groups containing an N-heterocycle (such as pyrrolidine or piperidine), as well as N-ethyl and N-methylsulfamoyl groups and other mixed N-alkylsulfamoyl groups.

The resulting compound of formula II can be purified by recrystallization from a suitable solvent or mixture of solvents. For example, combinations of ethereal and non-polar solvents, such as isopropyl ether/heptane as well as crystallization out of concentrated solutions of purely ethereal solvents such as tert-butyl methyl ether can be carried out.

Alternative Preparation of a Compound of Formula II

The starting aziridine can be protected with any suitable protecting group ($R_1$), for example, by treatment with a compound $R_1$—X wherein X is a leaving group, under standard conditions to provide the corresponding compound of formula II. For example, the reaction can be carried out in a suitable solvent in the presence of a base. Suitable solvents include aprotic solvents such as dichloromethane, tetrahydrofuran, ethyl ether, tert-butyl methyl ether, tetrahydropyran, 1,4-dioxane, 1,2-dichloroethane, and mixtures thereof. Suitable bases include trialkylamines such as triethylamine, N-methyl morpholine, quinuclidine, N-methylpiperidine, N,N-diisopropylethylamine, and N-methyl pyrrolidine; as well as other weak, non-nucleophilic bases such as, potassium carbonate and sodium bicarbonate. The reaction can conveniently be carried out at a temperature from about −10° C. to 40° C.

The resulting compound of formula II can be purified by recrystallization from a suitable solvent or mixture of solvents. For example, combinations of ethereal and non-polar solvents, such as ethyl ether, n-butyl ether, tetrahydrofuran, tetrahydropyran, 1,2-dimethoxyethane, hexanes, tert-butyl methyl ether, heptane, pentane, cyclohexane, toluene can be used.

Preparation of a Compound of Formula V:

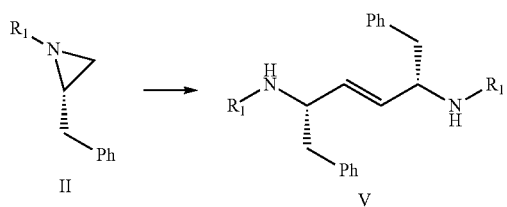

The starting aziridine can be dimerized by treatment with a non-nucleophilic amide base in a suitable solvent. Suitable solvents include ethers such as ethyl ether, tert-butyl methyl ether, n-butyl ether, tetrahydropyran, and tetrahydrofuran, as well as hydrocarbons such as hexanes and heptane, and mixtures thereof. Suitable non-nucleophilic amide base include lithium diisopropylamide, lithium 2,2,6,6-tetramethylpiperidide, lithium hexamethyldisilazide, sodium hexamethyldisilazide, potassium hexamethyldisilazide, lithium di-t-butylamide, and lithium isopropylcyclohexylamide. The reaction can conveniently be carried out at a temperature from about −78° C. to 22° C.

The resulting compound of formula V can be purified by recrystallization from a suitable solvent or mixture of solvents. For example, combinations of ethereal and non-polar solvents, such as ethyl ether, n-butyl ether, tetrahydrofuran, tetrahydropyran, 1,2-dimethoxyethane, and tert-butyl methyl ether can be used.

Preparation of a Compound of Formula VI:

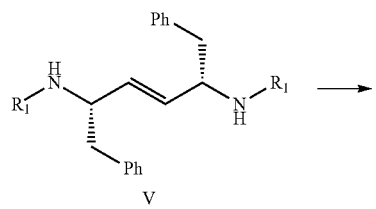

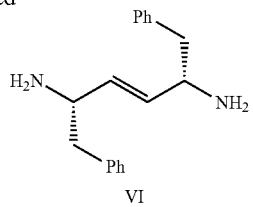

The starting compound of formula V can be deprotected under standard conditions to provide the corresponding compound of formula VI. The reaction can be carried out in a solvent that comprises an amine; for example, a monoamine such as ethanolamine, a diamine such as 1,3-diaminopropane, ethylenediamine, 1,2-diaminocyclohexane, 1,2-phenylenediamine, putrescene, or cadaverine, or a polyamine such as diethylenetriamine, triethylenetriamine, or polyethyleneimine. The solvent can also comprise toluene, anisole, or the like, or mixtures thereof. The reaction can conveniently be carried out at a temperature from about 100° C. to about 140° C.

Hydrogenation to Provide a Compound of Formula VII

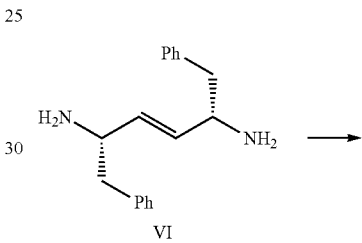

The starting alkene VI can be hydrogenated under standard conditions. For example, the hydrogenation can be carried out using a metal containing catalyst in an alcoholic solvent. Suitable solvents include methanol, ethanol, isopropanol, n-propanol, butanol, ethyl acetate, toluene, dioxane, and anisole, and mixtures thereof. Suitable catalysts include palladium on carbon, platinum on carbon, Raney nickel, Wilkinson's catalyst, and palladium hydroxide. The reaction can conveniently be carried out at a pressure from about ambient pressure to about 60 psi.

The compound of formula VII can conveniently be isolated by treatment with an acid in an organic solvent to provide a corresponding salt. Suitable acids include hydrochloric acid, hydrobromic acid, hydroiodic acid, and sulfuric acid. Suitable solvents include dichloromethane, ethyl ether, tetrahydrofuran, tert-butyl methyl ether, 1,4-dioxane, 1,2-dimethoxyethane, chloroform, 1,2-dichloroethane, toluene, and anisole, and mixtures thereof. The conversion to the salt can conveniently be carried out at a temperature from about −10° C. to about 40° C.

Preparation of a Compound of Formula VIII:

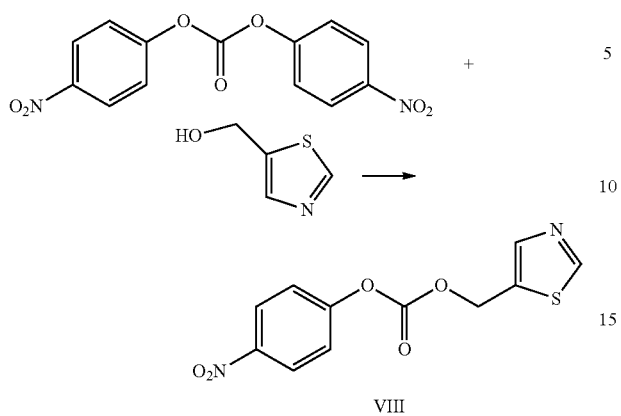

The mixed carbonate of formula VIII can be prepared by treating 5-hydroxymethylthiazole with a suitable carbonate or carbonate equivalent having a leaving group adjacent to the carbonyl carbon, such as phosgene in the presence of a base. For example, suitable carbonates include bis-(4-nitrophenyl) carbonate and disuccinimidyl carbonate. The reaction can conveniently be carried out in a suitable aprotic organic solvent, such as dichloromethane, tetrahydrofuran, 1,2-dichloroethane, or diethylether, or a mixture thereof. Suitable bases include trialkylamine bases, such as diisopropylethylamine, N-methyl morpholine, and triethylamine.

Preparation of a Compound of Formula IX or a Salt Thereof

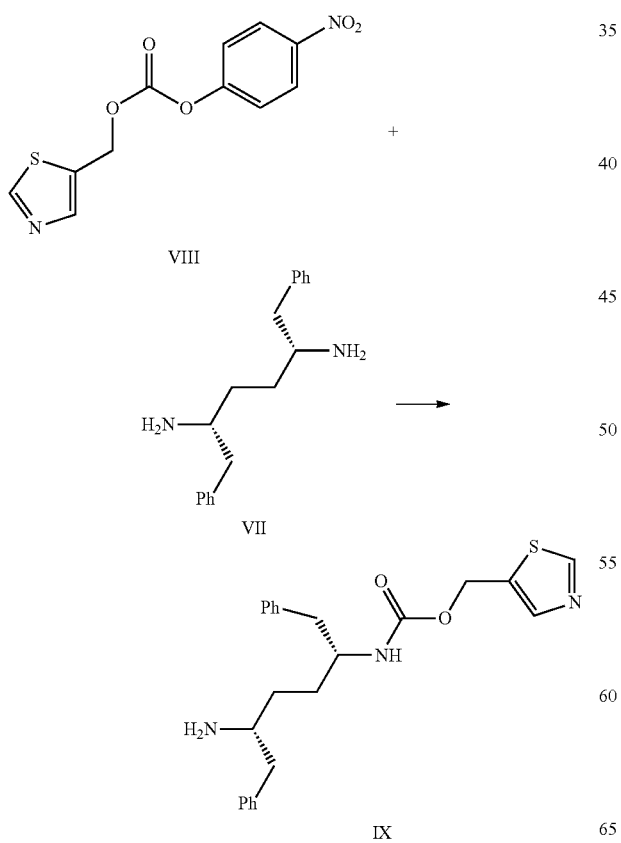

A compound of formula IX or a salt thereof can be prepared from a compound of formula VII or a salt thereof by treatment with a carbonate of formula VIII or a salt thereof in the presence of a suitable base in a suitable solvent. Suitable bases include carbonate bases (e.g. potassium carbonate) and trialkylamines (e.g. diisopropylethylamine, or N-methyl morpholine). Suitable solvents include solvents such as dichloromethane, tetrahydrofuran, 1,2-dichloroethane, isopropylacetate, and diethylether, and mixtures thereof.

Preparation of a Compound of Formula XI:

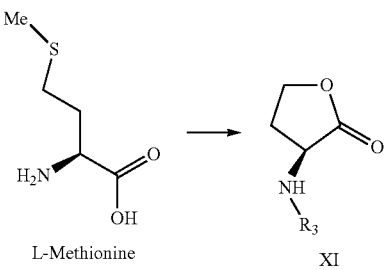

A compound of formula XI wherein $R_3$ is H or a salt thereof can be prepared by treating L-methionine with an alkylating agent in the presence of water and acetic acid. Suitable alkylating agents include alkyl bromides (bromoacetic acid), alkyl iodides, alkyl chlorides, and dimethyl sulfate. The reaction can conveniently be carried out in a solvent that comprises an alcohol (e.g. isopropanol), water, and acetic acid. The reaction can be carried out at a temperature from about 22° C. to about 90° C. A compound of formula XI wherein $R_3$ is a protecting group (e.g. a carbamate, amide, or benzyl protecting group) or a salt thereof can be prepared by protecting a corresponding compound of formula XI wherein $R_3$ is hydrogen to provide the compound of formula XI wherein $R_3$ is a protecting group or the salt thereof.

Preparation of a Compound of Formula XII:

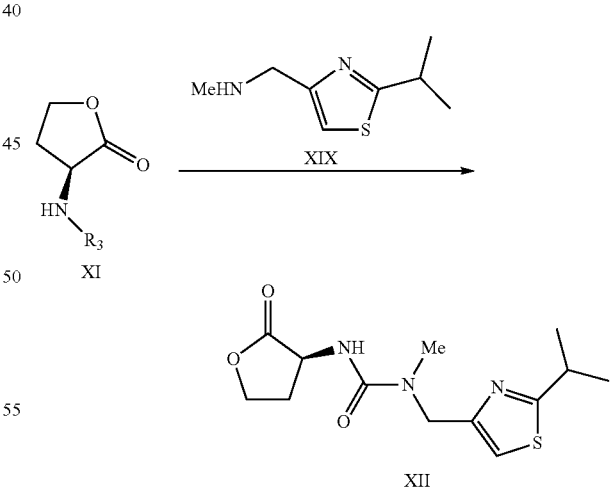

A compound of formula XII can be prepared by treating a compound of formula XI wherein $R_3$ is H or a protecting group (e.g. a carbamate, amide, or benzyl protecting group), or a salt thereof with a compound of formula XIX or a salt thereof, in an aprotic solvent at a temperature from about 0° C. to about 30° C. in the presence of a suitable base and a carbonyl source, such as CDI. When $R_3$ is a protecting group it can subsequently be removed to provide the compound of formula XII or the salt thereof. Suitable bases include metal hydrides (e.g. sodium hydride), and trialkylamines (e.g. diisopropylethylamine, triethylamine, N-methyl morpholine or DBU). Suitable aprotic solvents include tetrahydrofuran, 2-methyltetrahydrofuran, and dichloromethane, and mixtures thereof.

Preparation of a Compound of Formula XIII:

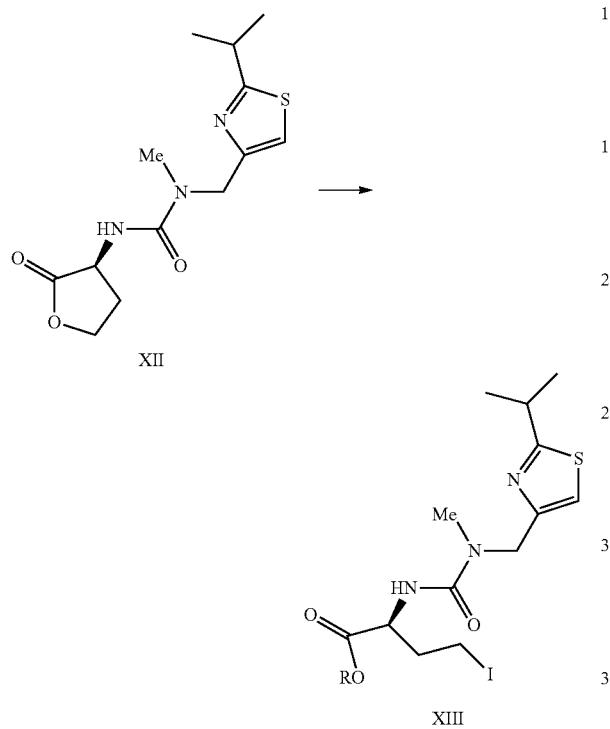

A compound of formula XIII can be prepared by treating a compound of formula XII or a salt thereof with a suitable iodide source (e.g. trimethylsilyl iodide, hydrogen iodide, or sodium iodide and trimethylsilyl chloride) in an aprotic solvent in the presence of an alcohol ROH to provide the compound of formula XIII wherein R is $(C_1\text{-}C_8)$alkyl. Suitable aprotic solvents include tetrahydrofuran, 2-methyltetrahydrofuran, dichloromethane, and acetonitrile, and mixtures thereof. The reaction can typically be carried out at a temperature from about 0° C. to about 22° C.

Preparation of a Compound of Formula XIV or a Salt Thereof:

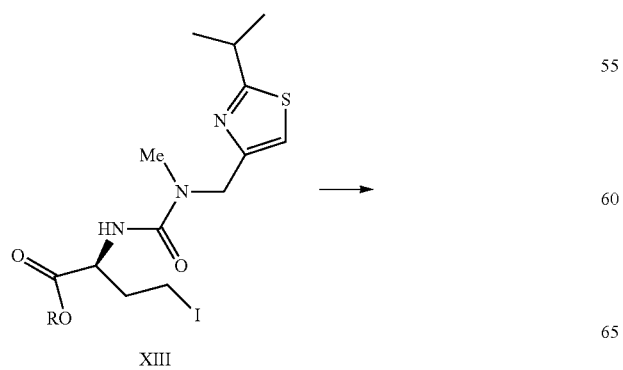

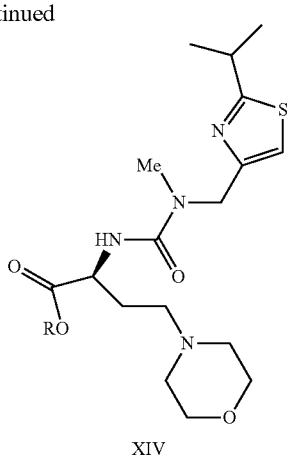

A compound of formula XIV or a salt thereof can be prepared by treating a compound of formula XIII wherein R is $(C_1\text{-}C_8)$alkyl with morpholine to provide the compound of formula XIV or the salt thereof. The resulting compound of formula XIV can be converted to a corresponding salt by treatment with an acid (e.g. an organic acid such as oxalic acid, citric acid, or fumaric acid, or a mineral acid) in an organic solvent. Suitable solvents include tert-butyl methyl ether, methylene chloride, tetrahydrofuran, acetone, acetonitrile, toluene, heptanes, isopropyl acetate, ethyl acetate and alcohols, and mixtures thereof. The salt formation can typically be carried out at a temperature from about 22° C. to about 60° C.

Preparation of a Compound of Formula X:

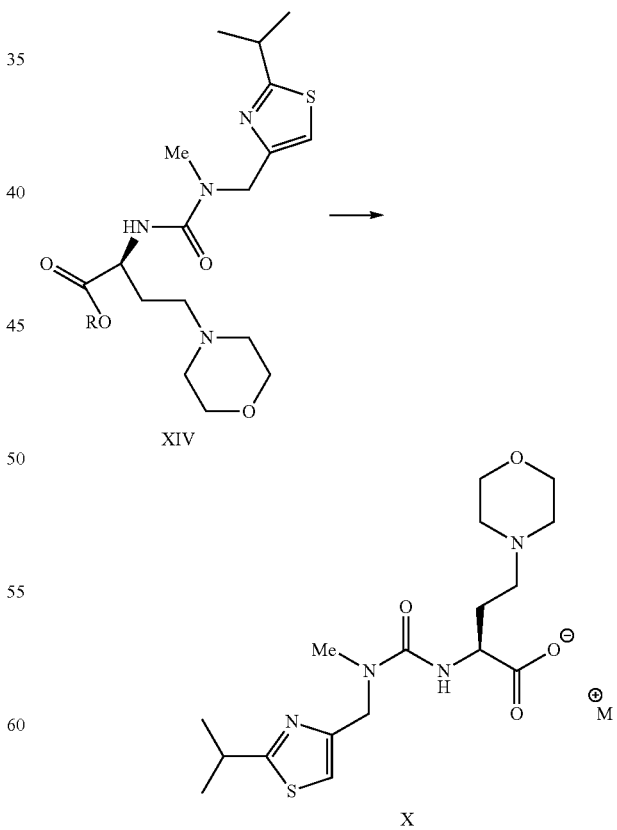

A compound of formula X wherein $M^+$ is a counterion, or a salt thereof, can be prepared by hydrolyzing an ester of formula XIV wherein R is $(C_1-C_8)$alkyl or a salt thereof under standard conditions. For example, the hydrolysis can be carried out in an aqueous solvent (e.g. water and dichloromethane) in the presence of a base (e.g. potassium hydroxide or lithium hydroxide) at a temperature from about −10° C. to about 28° C.

Preparation of a Compound of Formula I:

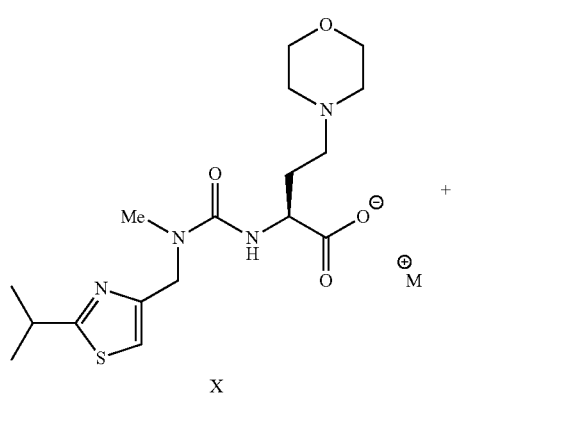

X

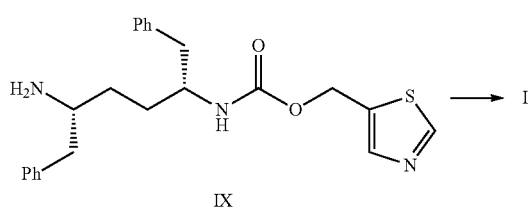

IX

A compound of formula I or a salt thereof can be prepared by coupling an acid salt of formula X wherein M+ is a counterion with an amine of formula IX to form the corresponding amide. This amide forming reaction can be carried out under standard conditions. For example, it can be carried out in a suitable organic solvent (e.g. dichloromethane) in the presence of a suitable coupling agent (e.g. EDC.HCl and HOBt). Other suitable amide coupling reagents and conditions are known in the field. The reaction can typically be carried out at a temperature from about −30° C. to about 20° C.

When carried out in dichloromethane or toluene or a mixture thereof, this coupling reaction unexpectedly provides improved results compared to the coupling in tetrahydrofuran that is described on page 254 of international patent application publication number WO 2008/103949. Accordingly, in one embodiment, the invention provides a process for preparing a compound of formula I comprising coupling an acid salt of formula X with an amine of formula IX or a salt thereof in dichloromethane or toluene or a mixture thereof. This reaction can conveniently be carried out in the presence of a coupling agent (e.g. EDC.HCl and HOBt) at a temperature from about −30° C. to about 20° C.

The resulting compound of formula I can be isolated using standard techniques. The compound of formula I can be isolated employing a solid support material as described in International Patent Application Publication Number WO 2009/135179

Alternative Preparation of a Compound of Formula I:

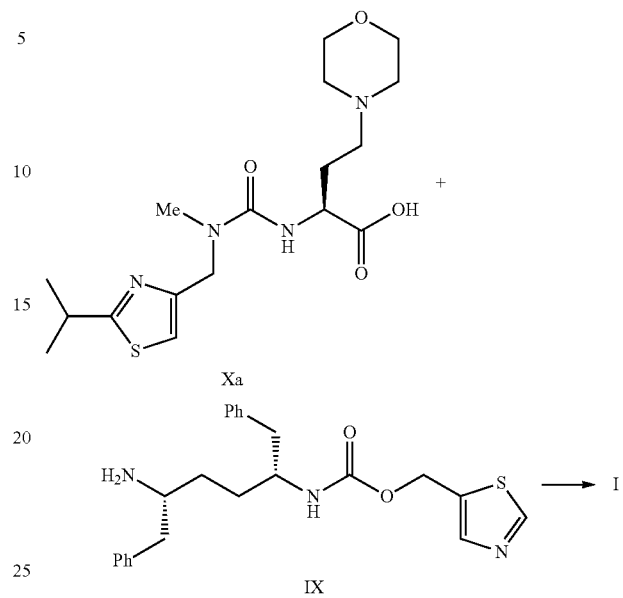

A compound of formula I or a salt thereof can be prepared by coupling an acid of formula Xa or a salt thereof with an amine of formula IX or a salt thereof to form the corresponding amide. This amide forming reaction can be carried out under standard conditions. For example, it can be carried out in a suitable organic solvent (e.g. dichloromethane) in the presence of a suitable coupling agent (e.g. EDC.HCl and HOBt). Other suitable amide coupling reagents and conditions are known in the field. The reaction can typically be carried out at a temperature from about −30° C. to about 20° C.

Alternative Preparation of a Compound of Formula XII

The compound of formula XII shown in Scheme III above can also be prepared as illustrated in Scheme V.

Scheme V

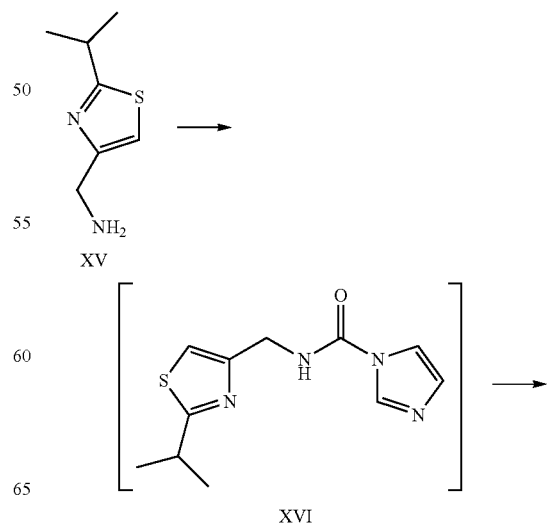

-continued

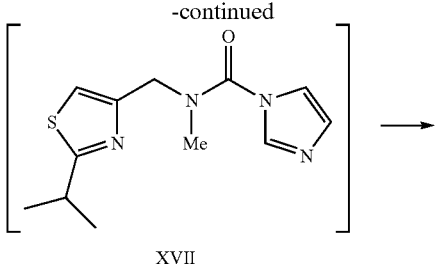

XVII

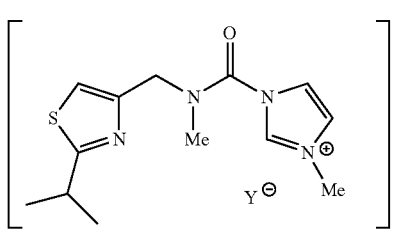

XVIII

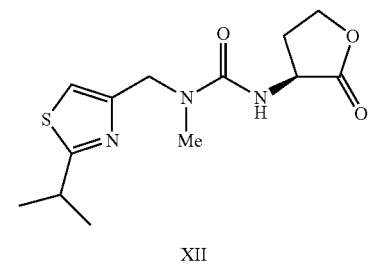

XII

Preparation of a Compound of Formula XII

The amine of formula XV or a salt thereof can be treated with carbonyldiimidazole, in the presence of a suitable base (e.g. a trialkylamine, such as triethylamine, N-methyl morpholine, diisopropylethylamine, or DBU; a hydride base, such as sodium hydride; or an amide base, such as LiHMDS) in an aprotic solvent (e.g. tetrahydrofuran, or 2-methyltetrahydrofuran) to provide the urea of formula XVI. Alkylation of the urea of formula XVI with a suitable methylating agent (e.g. methyl iodide) in the presence of a base in an aprotic solvent provides a compound of formula XVII. Further alkylation with a suitable methylating agent (e.g. methyl iodide) provides a salt of formula XVIII. Treatment of the salt of formula XVIII with an N-unprotected amino γ-lactone of formula XI or with a corresponding N-protected amino γ-lactone (e.g. a carbamate, amide or benzylamine) in a suitable aprotic solvent (e.g. tetrahydrofuran, or 2-methyltetrahydrofuran) in the presence of a suitable base (e.g. a trialkylamine, such as triethylamine, N-methyl morpholine, diisopropylethylamine, or DBU) provides the compound of formula XII. If an N-protected amino γ-lactone is utilized in the previously described step (i.e. $R_3$ is a protecting group), the resulting protected product can be deprotected to provide the compound of formula XII.

The invention will now be illustrated by the following non-limiting examples.

Example 1

Preparation of Protected (L)-Phenylalaninol IVa

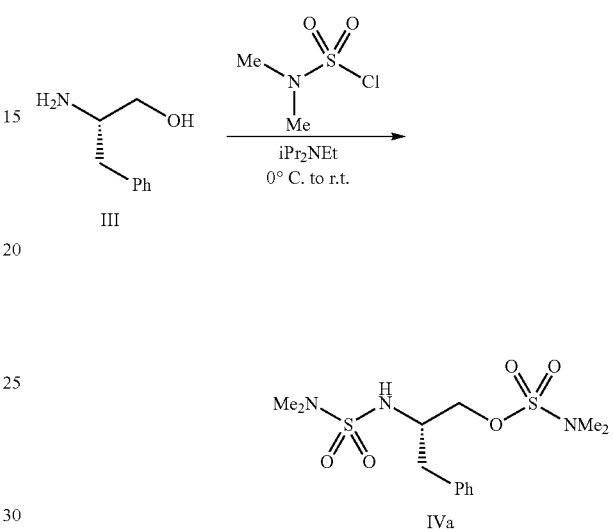

L-phenylalaninol III (5.0 g) was dissolved in dichloromethane (150 mL). The resulting solution was cooled to 0° C. and diisopropylethylamine (21.4 g) was charged to the reaction mixture, followed by N,N-dimethylsulfamoyl chloride (10 g). The reaction was warmed to room temperature and allowed to stir. After 20 hours, the reaction was quenched with saturated aqueous ammonium chloride (100 mL) and water (50 mL). The layers were then separated and the organic phase was washed with 1 M HCl (2×10 volumes) and water (2×50 mL). The organics were then dried over sodium sulfate. The solids were filtered off and the liquors were concentrated in vacuo to yield 97% of compound IVa as a yellow-orange oil. Compound IVa was then typically used without further purification. $^1$H NMR (CDCl$_3$) δ 7.26 (m, 5H), 4.94 (d, 1H, J=8 Hz), 3.75 (m, 1H), 3.57 (m, 2H), 2.94 (s, 6H), 2.85 (m, 2H), 2.54 (s, 6H).

Example 2

Preparation of (S)-2-benzyl-N,N-dimethylaziridine-1-sulfonamide IIa

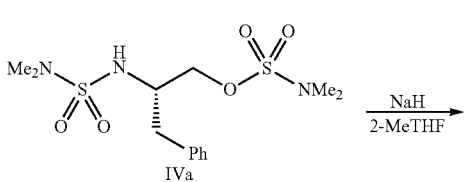

-continued

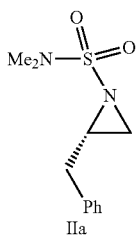
IIa

Protected amino alcohol IVa (10 g) was dissolved in 2-MeTHF (300 mL). The resulting solution was cooled to 0° C. Sodium hydride (2.0 g) was then charged portion-wise. The reaction was then warmed to room temperature and allowed to stir. After 4.5 hours, the reaction was cooled to 0° C. and quenched with saturated aqueous ammonium chloride solution (150 mL) and water (100 mL). The layers were separated and the organic layer was washed with 1M HCl (150 mL) followed by saturated aqueous NaCl (150 mL). The organics were dried over sodium sulfate. The solids were filtered off and the filtrate concentrated. Further purification can be done either by column chromatography eluting with 100% dichloromethane, or by recrystallization from MTBE/hexanes, ultimately yielding 64% of compound IIa as a white solid. $^1$H NMR (CDCl$_3$) δ 7.30 (m, 5H), 2.94 (dd, 1H, J=14, 5 Hz), 2.83 (m, 1H), 2.71 (dd, 1H, J=14, 7 Hz), 2.66 (s, 6H), 2.56 (d, 1H, J=7 Hz), 2.14 (d, 1H, J=4 Hz); $^{13}$C NMR (CDCl$_3$) δ 137.4, 129.3, 128.9, 127.2, 77.6, 77.3, 77.0, 40.6, 38.3, 38.1, 33.0.

Example 3

Alternative Preparation of (S)-2-benzyl-N,N-dimethylaziridine-1-sulfonamide IIa

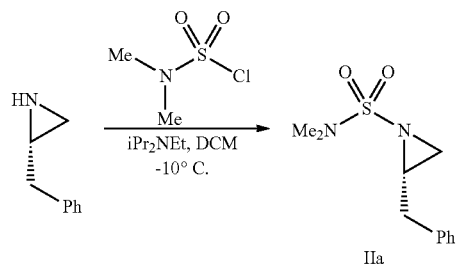 [SMILES: c1ccc(C[C@H]2CN2)cc1 ; CN(C)S(=O)(=O)Cl ; CN(C)S(=O)(=O)N1C[C@@H]1Cc1ccccc1]

To a cooled (−10° C.) solution of (S)-2-benzylaziridine (100 g, 0.751 mol) and N,N-dimethylsulfamoyl chloride (84.5 mL, 0.787 mol) in dichloromethane (100 mL) was added N,N-diisopropylethylamine (131 mL, 0.751 mol). The resulting yellow solution was stirred at −10° C. for a minimum of 16 hours. After this period, a 0.5M solution of citric acid (500 mL) was added and the phases were separated. The organic phase was then washed with 1.0 M sodium bicarbonate solution (500 mL). The organic phase was then solvent exchanged into tert-butyl methyl ether (500 mL). The solution was then cooled to 0° C., and heptane (100 mL) was added dropwise over a period of 2 hours. The mixture was then aged for an additional 2 hours at 0, and then cooled (−10° C.), to allowed compound IIa to precipitate out as a white, crystalline solid (27.8 g, 77%). Tlc assay: R$_f$: 0.53 (SiO$_2$; 1:1 heptane:ethyl acetate, KMnO$_4$). $^1$H NMR (400 MHz, CDCl$_3$): δ 7.20-7.29 (m, 5H), 2.94 (dd, J=14, 5 Hz, 1H), 2.80-2.88 (m, 1H), 2.70 (dd, J=14, 7 Hz, 1H), 2.66 (s, 6H), 2.56 (d, J=7 Hz, 1H), 2.14 (d, J=4 Hz, 1H). $^{13}$C NMR (100 MHz, CDCl$_3$): δ 137.4, 129.3, 128.9, 127.2, 40.6, 38.3, 38.1, 33.0.

Example 4

Preparation of Protected Diamine Va

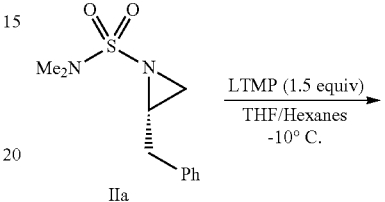

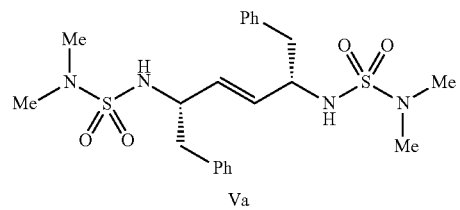
Va

To a cooled (0° C.) solution of 2,2,6,6-tetramethylpiperidine (5.5 mL) in tetrahydrofuran (14 mL) was added n-butyllithium (10M in hexanes, 3.1 mL). The resulting cloudy, yellow solution was warmed to 22° C. and allowed to stir at that temperature for 20 minutes.

To a cooled (−10° C.) cloudy solution of IIa (5.0 g) in tetrahydrofuran (7 mL) was added the preformed lithium tetramethylpiperidide (LTMP) dropwise by syringe pump (addition rate: 40 mL/hr, LTMP temperature: 22° C.). During the addition, the reaction gradually turns to a purple-brown solution. The reaction was then allowed to slowly warm to 0° C. over the course of 45 minutes. A 10% (w/v) solution of citric acid (15 mL) was then added to the cold reaction and the resulting bright-yellow solution was stirred vigorously at 0° C. for several minutes. The biphasic mixture was then diluted with ethyl acetate (75 mL) and the phases were separated. The organic phase was washed with 10% (w/v) citric acid (1×15 mL), saturated sodium bicarbonate (2×15 mL) and brine (1×15 mL). The organic phase was subsequently dried over sodium sulfate, filtered, and concentrated under reduced pressure to give a bright yellow solid. The crude mixture was suspended in hot tert-butyl methyl ether, cooled to −16° C., and filtered to give Va as a white powder (3.2 g, 64%). Tlc assay: R$_f$: 0.32 (SiO$_2$, 1:1 heptane:ethyl acetate, KMnO$_4$). $^1$H NMR (400 MHz, CDCl$_3$): δ 7.10-7.35 (m, 10H), 5.59 (s, 2H), 3.95-4.10 (m, 4H), 2.80 (ddd, J=22, 13, 6 Hz, 4H), 2.59 (s, 12H). $^{13}$C NMR (100 MHz, CDCl$_3$): δ 136.7, 132.0, 129.9, 128.9, 127.2, 57.0, 42.4, 38.1.

Example 5

Alternative Preparation of Protected Diamine Va

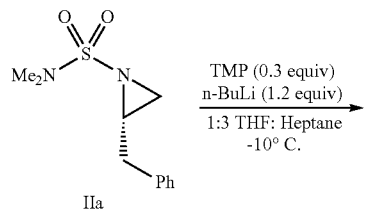

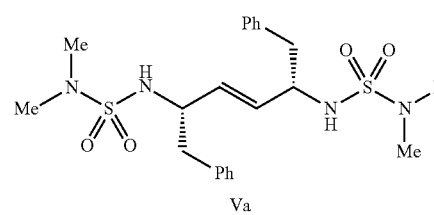

To a cooled (−10° C.) slurry of IIa (10.0 g) and 2,2,6,6-tetramethylpiperidine (2.1 mL) in 1:3 tetrahydrofuran:heptane (30 mL) was slowly added n-butyllithium (2.6M in hexanes, 19 mL) over the course of 3 hr. During the addition, the reaction gradually turned to a purple-brown solution; upon completion the resulting was stirred at that temperature for an additional 20 minutes.

Glacial acetic acid (4.0 mL) was then added to the cold reaction and the resulting bright-yellow suspension was stirred vigorously at 5° C. for several minutes. The mixture was then filtered and the solid material was washed with 3:1 t-butyl methyl ether:heptane (2×30 mL), water (3×30 mL), and again with 3:1 t-butyl methyl ether:heptane (2×30 mL). The wet cake was then thoroughly dried to give Va as a white powder (7.22 g, 72%). Tlc assay: R$_f$: 0.32 (SiO$_2$, 1:1 heptane:ethyl acetate, KMnO$_4$). $^1$H NMR (400 MHz, CDCl$_3$): δ 7.10-7.35 (m, 10H), 5.59 (s, 2H), 3.95-4.10 (m, 4H), 2.80 (ddd, J=22, 13, 6 Hz, 4H), 2.59 (s, 12H). $^{13}$C NMR (100 MHz, CDCl$_3$): δ 136.7, 132.0, 129.9, 128.9, 127.2, 57.0, 42.4, 38.1.

Example 6

Preparation of Unsaturated Diamine VI

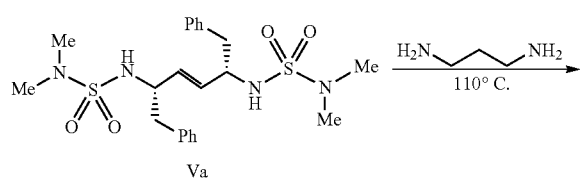

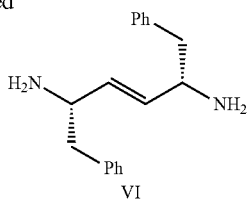

A solution of the protected diamine Va (2.0 g) in 1,3-diaminopropane (4 mL) was heated to 110° C. and stirred at that temperature for 90 minutes. After cooling the yellow solution to 22° C., water (16 mL) was added followed by dichloromethane (20 mL). The phases were separated and the aqueous phase was washed with an additional portion of dichloromethane (1×10 mL). The combined organic phases were dried over sodium sulfate, filtered, and concentrated under reduced pressure to give VI as a thick, yellow oil (1.1 g, 100%). This material was used directly in the next reaction without further purification. Tlc assay: R$_f$: 0.61 (SiO$_2$, 4:1 CH$_2$Cl$_2$:CH$_3$OH w/5% Et$_3$N, KMnO$_4$). $^1$H NMR (400 MHz, CDCl$_3$): δ 7.10-7.35 (m, 10H), 5.60 (dd, J=4, 2 Hz, 2H), 3.50-3.60 (br, 2H), 2.85 (dd, J=13, 5 Hz, 2H), 2.60 (13, 8 Hz, 2H), 1.15 (br, 4H). $^{13}$C NMR (100 MHz, CDCl$_3$): δ 139.0, 134.1, 129.7, 128.6, 126.5, 54.9, 44.9.

Example 7

Preparation of Compound VII

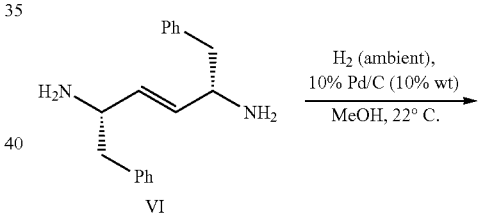

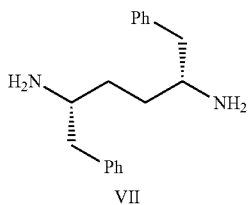

To a solution of unsaturated diamine VI (1.1 g) in methanol (8.2 mL) was added 10% palladium on carbon (110 mg, 10 wt %). The resulting black suspension was purged with hydrogen gas and held under a hydrogen atmosphere (balloon) for 16 hours. The reaction was then filtered through celite and concentrated under reduced pressure to provide VII as a thick, yellow oil (1.11 g, 100%). This material was carried on to the next reaction without further purification. Tlc assay: R$_f$: 0.60 (SiO$_2$, 4:1 CH$_2$Cl$_2$:CH$_3$OH w/5% Et$_3$N, KMnO$_4$). $^1$H NMR (400 MHz, CDCl$_3$): δ 7.15-7.35 (m, 10H), 2.95-3.05 (m, 2H), 2.82 (dd, J=13, 5 Hz, 2H), 2.50 (dd, J=13, 9 Hz, 2H), 1.45-

1.66 (m, 4H), 1.36 (br, 4H). $^{13}$C NMR (100 MHz, CDCl$_3$): δ 139.7, 129.5, 128.7, 126.5, 53.2, 45.1, 34.6.

Example 8

Preparation of Diamine-Dihydrogen Chloride VIIa

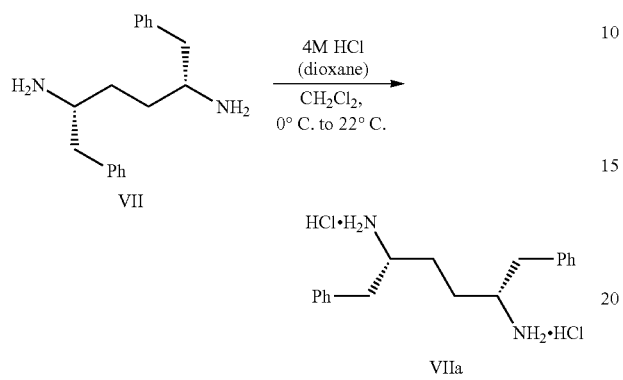

To a cooled (0° C.) solution of VII (1.11 g) in dichloromethane (14 mL) was added a solution of 4M hydrochloric acid in dioxane (2.6 mL). The resulting pale-pink suspension was allowed to warm to 22° C. and was stirred at that temperature for 90 minutes. The mixture was then filtered; the precipitate was washed with copious amounts of dichloromethane and dried in vacuo to provide VIIa as a pale-pink powder (1.32 g, 94% from V). $^1$H NMR (400 MHz, D$_2$O): δ 7.10-7.35 (m, 10H), 3.38-3.48 (m, 2H), 2.92 (dd, J=14, 7 Hz, 2H), 2.76 (dd, J=14, 8 Hz, 2H), 1.58-1.74 (m, 4H).

Example 9

Preparation of Carbonate VIII

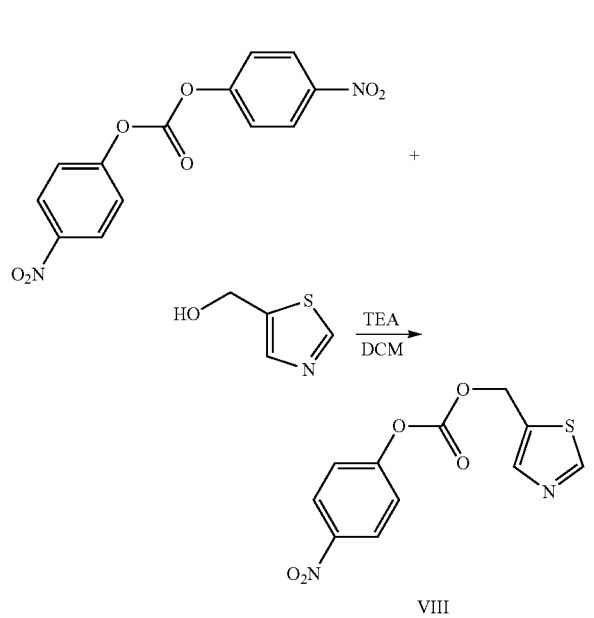

5-Hydroxymethylthiazole (5 kg) was dissolved in dichloromethane (210 kg). To this solution was added bis-(4-nitrophenyl)carbonate (15 kg) and triethylamine (7.5 kg). The reaction mixture was allowed to stir overnight. Upon reaction completion, the reaction mixture was washed with 1.0 M aqueous K$_2$CO$_3$ solution (50 kg) to fully remove 4-nitrophenol. The organic layer was then washed with 1.0 M aqueous citric acid until the pH of the organic solution was less than 8. The organic layer was dried over Na$_2$SO$_4$. The solids were then filtered off and the organic layer was solvent exchanged into isopropyl acetate and concentrated to a volume of approximately 4 volumes. To this solution was slowly added n-heptane (100 L) and allowed to age over a period of 5 or more hours. This affords VIII as a solid which can subsequently be isolated via filtration. $^1$H NMR (CDCl$_3$) δ 8.89 (s, 1H), 8.26 (d, 2H), 7.99 (s, 1H), 7.37 (d, 2H), 5.51 (s, 2H).

Example 10a

Preparation of Mono-Carbamate Hydrochloride IXa

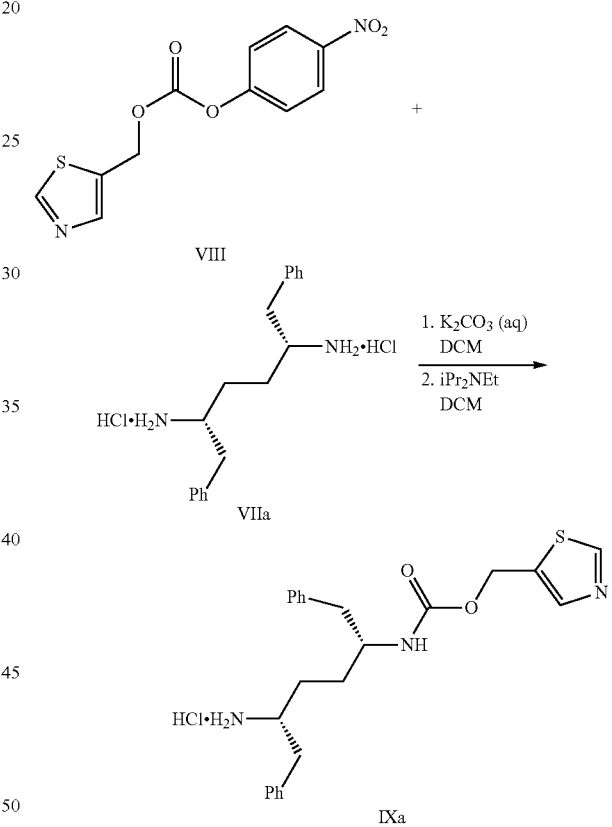

Diamine-dihydrochloride VIIa (237 kg), aqueous potassium carbonate (1M, 27 kg), and dichloromethane (68 kg) were agitated for 1 hour at 20° C. The dichloromethane layer was separated, dried over sodium sulfate (7.1 kg), and filtered to afford the diamine freebase. To this solution was charged additional dichloromethane (66 kg) and mixed-carbonate VIII (1.95 kg). Once all solids had dissolved, diisopropylethylamine (1.1 kg, 8.3 mol) was added and the reaction monitored by tlc assay (SiO$_2$, 80% ethyl dichloromethane in methanol as eluant, product R$_f$=0.73, visualization by UV). The reaction contents were washed with 0.25N aqueous NaOH until the presence of residual VIII and 4-nitrophenol were not detected by tlc assay. The organic layer was washed with water, dried over sodium sulfate (7 kg), filtered, concentrated and dissolved into isopropyl acetate (about 50 L) and diluted with dichloromethane (47 kg). To this solution was charged HCl (1.88 kg 4N HCl in dioxane, about 8.2 mol HCl) to induce precipitation. The product IXa was filtered and rinsed with isopropyl acetate (21 kg) and dried under vacuum to afford a white powder (2.57 kg, 83% yield). $^1$H NMR (CD$_3$OD) δ 9.0 (s, 1H), 7.8 (s, 1H), 7.4-7.14 (m, 10H), 5.2 (d, 1H), 4.8 (s, 5H) 3.7 (m, 1H), 3.6 (m, 1H), 3.3 (s, 1H), 2.6-2.8 (m, 2H), 1.8-1.4 (m, 4H). $^{13}$C NMR (CD$_3$OD) δ 154.4, 143.2, 129.6, 128.0, 126.0, 58.0, 52.4, 44.3, 41.6, 33.8, 30.5.

Example 10b

Preparation of Mono-Carbamate Hydrochloride IXa

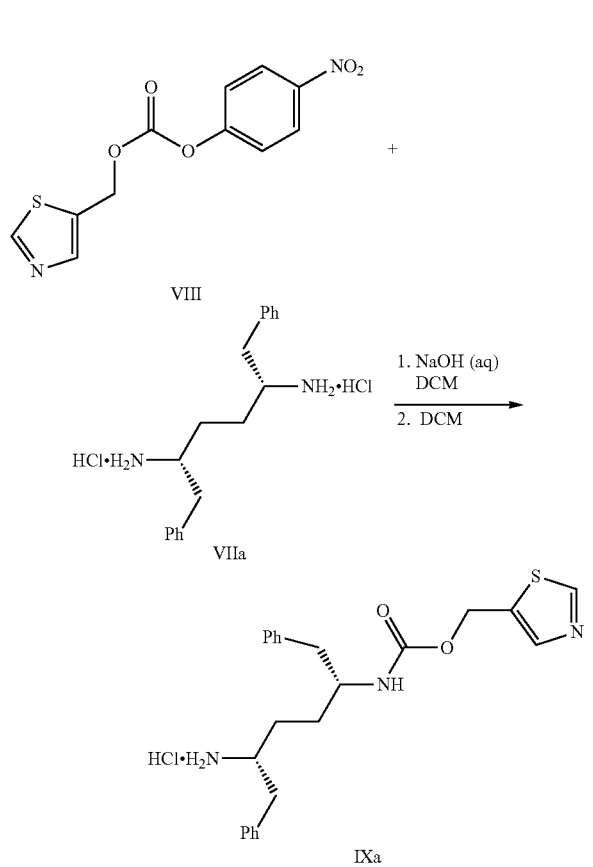

Diamine-dihydrochloride VIIa (2.0 g), aqueous sodium hydroxide (3M, 4.1 g), and dichloromethane (13.3 g) were agitated for 1 hour at 20° C. The dichloromethane layer was separated and subsequently washed with water (10 g) to afford the diamine freebase. To this solution was charged additional dichloromethane (26.6 g) and mixed-carbonate VIII (1.72 g). The resulting solution was heated to 40° C. and held at that temperature until the reaction was deemed complete by HPLC. The solvent was then removed in vacuo, co-distilled with tetrahydrofuran (17.8 g) and then rediluted with tetrahydrofuran (35.6 g). To this solution was then added concentrated hydrochloric acid (12M, 0.588 g) to induce precipitation. The product IXa was filtered, rinsed with 1% H$_2$O in 1:1 THF:CH$_2$Cl$_2$ (2×40 mL) and dried under vacuum to afford a white powder (2.15 g, 82% yield). $^1$H NMR (CD$_3$OD) δ 9.0 (s, 1H), 7.8 (s, 1H), 7.4-7.14 (m, 10H), 5.2 (d, 1H), 4.8 (s, 5H) 3.7 (m, 1H), 3.6 (m, 1H), 3.3 (s, 1H), 2.6-2.8 (m, 2H), 1.8-1.4 (m, 4H). $^{13}$C NMR (CD$_3$OD) δ 154.4, 143.2, 129.6, 128.0, 126.0, 58.0, 52.4, 44.3, 41.6, 33.8, 30.5.

Example 11

Preparation of Amino Lactone XIa

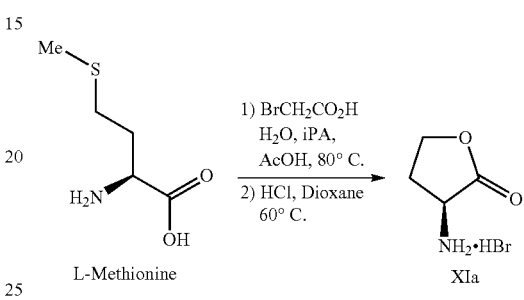

To a solution of L-methionine (46 kg) in water (69 kg, at ambient temperature was charged bromoacetic acid (46.0 kg), 2-propanol (69.0 kg) and acetic acid (69.0 kg). The resulting mixture was heated to reflux (85° C. to 95° C.) and agitated at this temperature until the reaction was judged complete by $^1$H NMR. The mixture was concentrated under reduced pressure and co-evaporated with 2-propanol. 2-Propanol (161.0 kg) was charged to the concentrated mixture, followed by a slow addition of 10 wt % HCl/dioxane solution (102 kg) at ambient temperature. The resulting slurry was heated to about 60° C. and agitated for about 4 hours. The pot temperature was adjusted to about 22° C. and agitated for about 2 hours. The product XIa was filtered, washed with two portions of 2-propanol (28 kg each portion) and dried under vacuum at 40° C. to afford white to off-white solid (39.3 kg, 70% yield). $^1$H NMR (D$_2$O) δ 4.79 (s, 2H), 4.61 (dd, 1H), 4.49-4.41 (m, 2H), 2.80 (m, 1H), 2.42 (m, 1H).

Example 12

Preparation of Urea XII

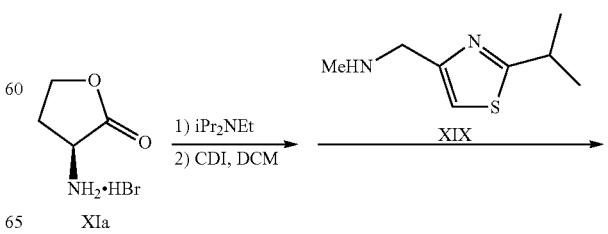

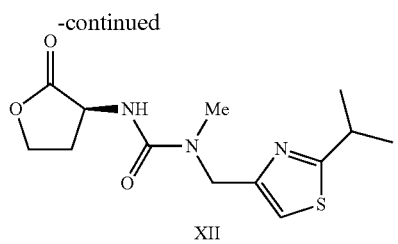

To a slurry of (L)-amino lactone XIa 31.5 kg) in dichloromethane (105 kg) was charged diisopropylethylamine (28.8 kg). The reaction mixture was cooled to about 10° C. and carbonyldiimidazole (27.1 kg) was added portion-wise while the content temperature was maintained at less than or equal to 25° C. The resulting mixture was agitated until the reaction was judged complete. Methyl aminomethyl thiazole XIX (21.0 kg) was charged maintaining content temperature at less than or equal to 25° C. and agitated. Once complete, the reaction mixture was washed with water (63.0 kg), then two times with 20 wt % aqueous citric acid solution (63.0 kg). All the aqueous layers were combined and extracted with dichloromethane (63.0 kg). The organic layers were combined and washed once with 8 wt % aqueous sodium bicarbonate solution (63.0 kg) and once with water (63.0 kg). The organic layer was concentrated under reduced pressure to 3 volumes and co-evaporated with dichloromethane. The product XII was discharged as a stock solution in dichloromethane (33.4 kg, 91% yield). $^1$H NMR (CDCl$_3$) δ 7.02 (s, 1H), 4.55-4.41 (m, 4H), 4.27 (m, 1H), 3.29 (septets, 1H), 2.98 (s, 3H), 2.78 (m, 1H), 2.20 (m, 1H), 1.38 (d, 6H).

Example 13

Preparation of L-Thiazole Morpholine Ethyl Ester Oxalate Salt XIVa

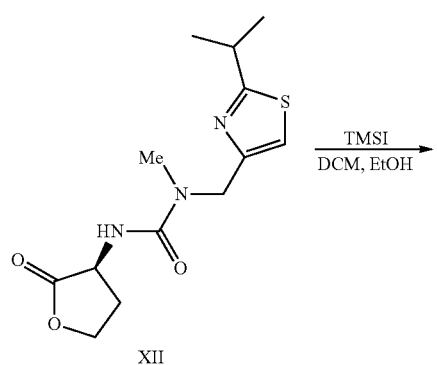

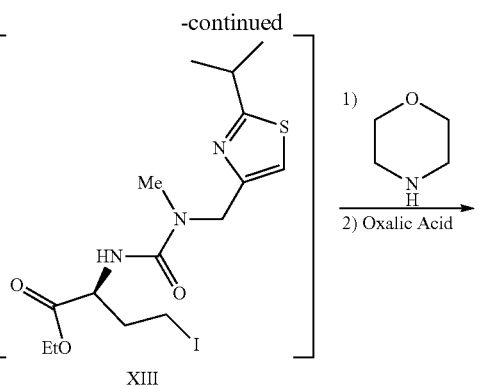

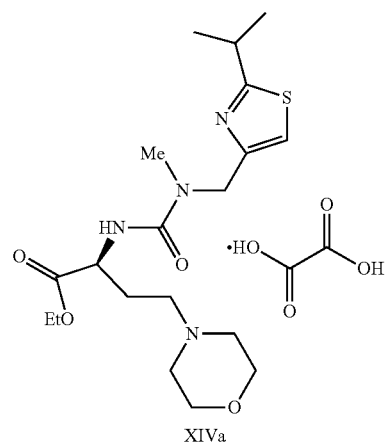

To a solution of (L)-thiazole amino lactone XII (33.4 kg) in dichloromethane (89.5 kg) was charged dichloromethane (150 kg) and absolute ethanol (33.4 kg). The content temperature was then adjusted to about 10° C., followed by slow addition of TMSI (78.8 kg) while the content temperature was maintained at less than or equal to 22° C. and agitated until the reaction was judged complete. The content temperature was adjusted to about 10° C., followed by a slow addition of morpholine (49.1 kg) while the content temperature was maintained at less than or equal to 22° C. Once complete, the reaction mixture was filtered to remove morpholine.HI salt and the filter cake was rinsed with two portions of dichloromethane (33.4 kg). The filtrate was washed twice with water (100 kg). The organic layer was concentrated under vacuum to dryness. Acetone (100 kg) was then charged to the concentrate and the solution was concentrated under reduced pressure to dryness. Acetone (233.8 kg) was charged to the concentrate, followed by a slow addition of the solution of oxalic acid (10 kg) in acetone (100 kg). The resulting slurry was refluxed for about 1 hour before cooling down to about 3° C. for isolation. The product XIVa was filtered and rinsed with acetone (66.8 kg) and dried under vacuum at 40° C. to afford a white to off-white solid (40 kg, 71% yield). $^1$H NMR (CDCl$_3$) δ 7.00 (s, 1H), 6.35 (broad s, 1H), 4.60-4.40 (m, 3H), 4.19 (quartets, 2H), 4.00-3.90 (m, 4H), 3.35-3.10 (m, 7H), 3.00 (s, 3H), 2.40-2.30 (m, 1H), 2.15-2.05 (m, 1H), 1.38 (d, 6H), 1.25 (triplets, 3H).

Example 14

Preparation of Compound I

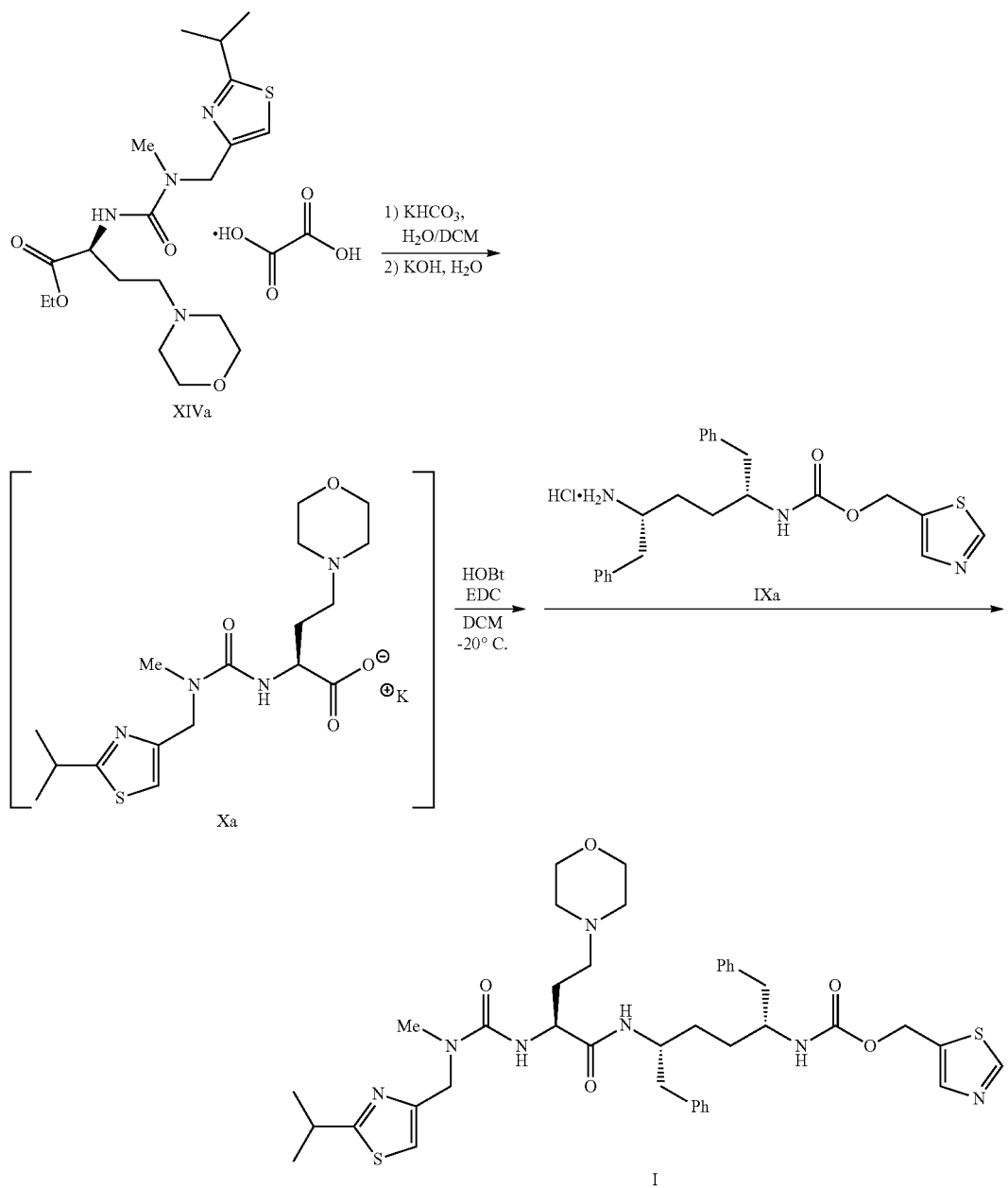

To the solution of L-thiazole morpholine ethyl ester oxalate salt XIVa (35.6 kg) in water (66.0 kg) was charged dichloromethane (264 kg), followed by a slow addition of 15 wt % KHCO$_3$ solution (184.8 kg). The resulting mixture was agitated for about 1 hour. The layers were separated and the organic layer was washed with water (132 kg). The organic layer was concentrated under vacuum to dryness. Water (26.5 kg) was charged and the content temperature was adjusted to about 10° C., followed by slow addition of 45% KOH solution (9.8 kg) while maintaining the content temperature at less than or equal to 20° C. The mixture was agitated at less than or equal to 20° C. until the reaction was judged complete by HPLC. The reaction mixture was concentrated under vacuum to dryness and co-evaporated five times with dichloromethane (132 kg each time) under reduced pressure to dryness. Co-evaporation with dichloromethane (132 kg) was continued until the water content was <4% by Karl Fischer titration. Additional dichloromethane (264 kg) was charged and the content temperature was adjusted to −18° C. to −20° C., followed by addition of monocarbamate.HCl salt IXa (26.4 kg). The resulting mixture was agitated at −18° C. to −20° C. for about 1 hour. HOBt (11.4 kg) was charged and the reaction mixture was again agitated at −18° C. to −20° C. for about 1 hour. A pre-cooled solution (−20° C.) of EDC.HCl (21.4 kg) in dichloromethane (396 kg) was added to the reaction mixture while the content temperature was maintained at less than or equal to −20° C. The reaction mixture was agitated at −18° C. to −20° C. until the reaction was judged complete. The content temperature was adjusted to about 3° C. and the reaction mixture quenched with a 10 wt % aqueous citric acid solution (290 kg). The layers were separated and the organic layer was washed once with 15 wt % potassium bicarbonate solution (467 kg) and water (132 kg). The organic layer was concentrated under reduced pressure and then co-evaporated with absolute ethanol. The product I was isolated as the stock solution in ethanol (35.0 kg product, 76.1% yield). $^1$H NMR ($^d$DMSO) δ 9.05 (s, 1H), 7.85 (s, 1H), 7.52 (d, 1H), 7.25-7.02 (m, 12H), 6.60 (d, 1H), 5.16 (s, 2H), 4.45 (s, 2H), 4.12-4.05 (m, 1H), 3.97-3.85 (m, 1H), 3.68-3.59 (m, 1H), 3.57-3.45 (m, 4H), 3.22 (septets, 1H), 2.88 (s, 3H), 2.70-2.55 (m, 4H), 2.35-2.10 (m, 6H), 1.75 (m, 1H), 1.62 (m, 1H), 1.50-1.30 (m, 4H), 1.32 (d, 6H). $^{13}$C NMR (CD$_3$OD) δ 180.54, 174, 160.1, 157.7, 156.9, 153.8, 143.8, 140.1, 140.0, 136.0, 130.53, 130.49, 129.4, 127.4, 127.3, 115.5, 67.7, 58.8, 56.9, 55.9, 54.9, 53.9, 51.6, 49.8, 42.7, 42.0, 35.4, 34.5, 32.4, 32.1, 29.1, 23.7.

Example 15

Alternative Preparation of Urea XII

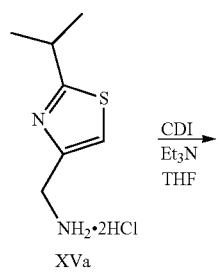

XVa

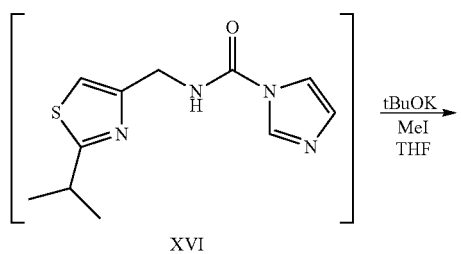

XVI

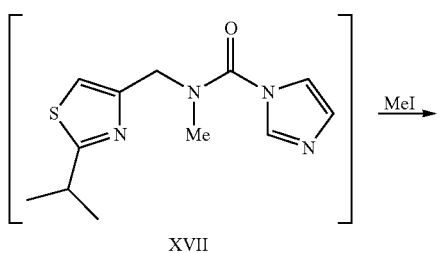

XVII

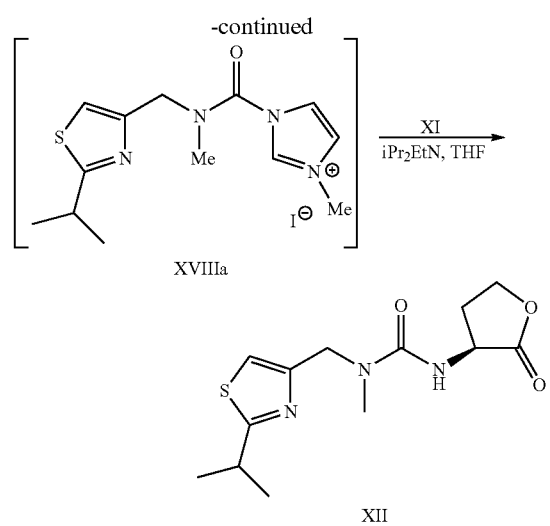

XVIIIa

XII

A urea of formula XII can also be prepared as described in steps a-d below.

a. To a slurry of carbonyldiimidazole (8.5 g, 0.052 mol, 1.2 eq.) in tetrahydrofuran (100 g) at about 10° C. was charged triethylamine (6.6 g, 0.065 mol, 1.5 eq.) while the reaction temperature was maintained at about 10° C. The resulting slurry was charged in portions with starting amino isopropylthiazole diHCl, (XVa, 10 g, 0.044 mol) with the pot temperature maintained at about 10° C. Once the addition was complete, the pot temperature was allowed to warm to ambient temperature and the reaction mixture was agitated at this temperature until the reaction was judged complete by HPLC (target: starting material≤1%). Once complete, the triethylamine HCl salt was filtered off. The wet filter cake was washed with THF (80 kg) and the filtrate was concentrated under vacuum at about 40° C. and co-evaporated with ethyl acetate (50 kg). To the resulting slurry was charged with ethyl acetate (20 kg), then cooled to about 0° C. and agitated at this temperature for about 1 hour. The product was filtered off and washed with heptane (20 kg). The filter cake was pulled dry in the filter under vacuum.

b. The above wet filter cake was slurried up in tetrahydrofuran (80 g) and the pot temperature was adjusted to about 0° C. To this slurry, tert-BuOK (6.9 g, 0.061 mol, 1.4 eq.) was slowly charged while the reaction temperature was maintained at about 0° C., followed by addition of methyl iodide (8.7 g, 0.061 mol, 1.4 eq.) at about 0° C. Once the addition was complete, the reaction mixture was allowed to warm to ambient temperature and agitated at this temperature until the reaction was judged complete by HPLC (target: product≥70%). Once complete, the reaction mixture was adjusted to about 3° C. and agitated at this temperature for about 1 hour. The potassium iodide salt was filtered off and the filter cake was washed with THF (20 g). The mother-liquor containing product was collected and carried forward to the next step.

c. To the above mother-liquor, methyl iodide was charged (18.6 g, 0.131 mol, 3 eq.) and the reaction mixture was warmed to about 35° C. and agitated at this temperature until the reaction was judged complete by HPLC (target: starting material≤1%, approximately 24 hours). Once complete, the reaction mixture was adjusted to ambient temperature and filtered. The product filter cake was washed with THF (20 g). The filter cake was pulled dry in the filter under vacuum.

d. To the above wet filter cake was charged THF (80 g), followed by portion-wise addition of L-amino lactone, XI (7 g, 0.038 mol, 0.9 eq.). To the resulting mixture, diisopropylethylamine (8.5 g, 0.066 mol, 1.5 eq.) was charged slowly while the reaction temperature was maintained below 30° C. Once the addition was complete the reaction temperature was adjusted to ambient and agitated until the reaction was judged complete by HPLC (target: starting material≤1%, approximately 48 hours). Once complete, the reaction mixture was concentrated under vacuum to approximately 3 volumes with the bath temperature set at maximum (40° C.). The concentrate was then adjusted to ambient and charged with methylene chloride (50 g). The resulting organic solution was washed with 20% citric acid solution (30 g) and then water (30 g). The aqueous layers were combined and back extracted with methylene chloride (50 g). The organic layers were combined and concentrated under reduced pressure to about 3 volumes with bath temperature set at ≤40° C. The concentration was repeated until KF limit was met (target: KF≤0.5%). Once KF limit was met, the product XII was discharged as a stock solution in methylene chloride (5.8 g, 45% yield). $^1$H NMR (CDCl$_3$) δ 7.02 (s, 1H), 4.55-4.41 (m, 4H), 4.27 (m, 1H), 3.29 (septets, 1H), 2.98 (s, 3H), 2.78 (m, 1H), 2.20 (m, 1H), 1.38 (d, 6H).

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula IVa:

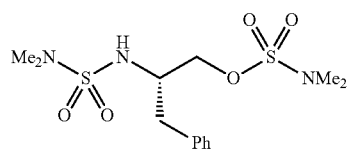

IVa or a salt thereof.

2. A compound of formula Va:

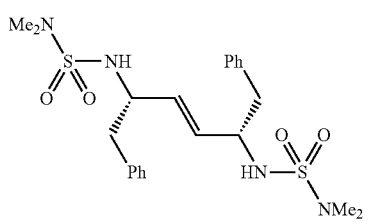

Va or a salt thereof.

3. A compound of formula XVI, or XVII:

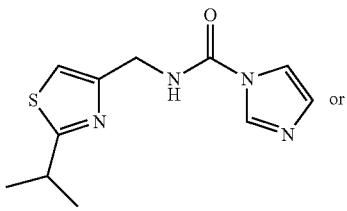

XVI or

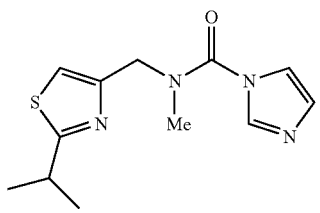

XVII or a salt thereof.

4. A salt of formula XVIII:

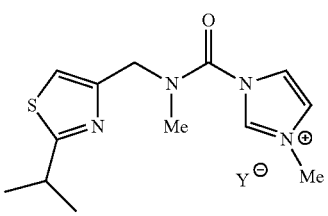

XVIII wherein Y is a suitable counterion.

* * * * *